United States Patent
Mandal et al.

(10) Patent No.: US 8,285,523 B2
(45) Date of Patent: Oct. 9, 2012

(54) ELECTRONIC SYSTEM FOR MODELING CHEMICAL REACTIONS AND BIOCHEMICAL PROCESSES

(75) Inventors: Soumyajit Mandal, Cambridge, MA (US); Rahul Sarpeshkar, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 348 days.

(21) Appl. No.: 12/575,291

(22) Filed: Oct. 7, 2009

(65) Prior Publication Data
US 2010/0211364 A1  Aug. 19, 2010

Related U.S. Application Data

(60) Provisional application No. 61/207,962, filed on Feb. 17, 2009, provisional application No. 61/175,285, filed on May 4, 2009.

(51) Int. Cl.
*G06F 17/10*  (2006.01)
*G06G 7/48*  (2006.01)

(52) U.S. Cl. .............. 703/2; 703/11; 703/12; 703/14
(58) Field of Classification Search .......... 703/2, 11–16
See application file for complete search history.

(56) References Cited

U.S. PATENT DOCUMENTS

| | | | | |
|---|---|---|---|---|
| 5,914,891 | A * | 6/1999 | McAdams et al. | 703/11 |
| 7,844,431 | B2 * | 11/2010 | Paxson et al. | 703/11 |
| 2004/0139040 | A1 * | 7/2004 | Nervegna et al. | 706/15 |
| 2005/0071142 | A1 * | 3/2005 | Chen et al. | 703/11 |
| 2005/0120030 | A1 * | 6/2005 | Varpela et al. | 707/100 |
| 2005/0187745 | A1 * | 8/2005 | Lurie et al. | 703/11 |
| 2005/0192756 | A1 * | 9/2005 | Varpela et al. | 702/19 |
| 2007/0212624 | A1 * | 9/2007 | Philippou et al. | 430/30 |

OTHER PUBLICATIONS

Mandal et al, Log-Domain Circuit Models of Chemical Reactions, IEEE International Symposium on Circuits and Systems, Jun. 2009, pp. 2697-2700.*
Davies, S.W., The Genetic Translator, ASM Conferences, Bio-, Micro-, and Nanosystems, 2003, pp. 13-14.*
Simpson et al, Engineering in the Biological Substrate: Information Processing in Genetic Circuits, Proceedings of the IEEE, vol. 92, No. 5, 2004, pp. 848-863.*
Nagaraj et al, A Genetic Differential Amplifier: Design, Simulation, Construction, and Testing, Bio Micro and Nanosystems Conference, 2006, p. 36.*
De Rubertis et al, Genetic Circuit Design from an Electronics Perspective, Proceedings of the IEEE-EMBS Special Topic Conference on Molecular, Cellular and Tissue Engineering, 2002, pp. 145-146.*
Igor Jurisica et al; Knowledge Discovery in Proteomics, Theoretical Models of Biological Systems; 2005; pp. 250-252.

* cited by examiner

*Primary Examiner* — Russell Frejd
(74) *Attorney, Agent, or Firm* — Quarles & Brady LLP

(57) ABSTRACT

A system for modeling chemical reactions using analog or hybrid-analog-digital electronic circuits. The system exploits similarities between the kinetic rates of chemical reaction and the rates governing current flow in electronic devices such as bipolar junction transistors (BJTs) and metal oxide semiconductor field effect transistors (MOSFETs) operating at sub-threshold conditions. These devices, which accurately model the stochastics of chemical processes, can be networked into large arrays to model chemical reaction networks, including biochemical reactions and genetic processes such as activation, induction, transcription, and translation.

66 Claims, 15 Drawing Sheets

ELECTRONIC SYSTEM FOR MODELING CHEMICAL REACTIONS AND BIOCHEMICAL PROCESSES

CROSS-REFERENCE TO RELATED APPLICATIONS

This application is based on, claims the benefit of, and incorporates herein by reference U.S. Provisional Application Ser. No. 61/207,962, filed Feb. 17, 2009, and entitled "Log-Domain Circuit Models of Chemical Reactions" and U.S. Provisional Application Ser. No. 61/175,285, filed May 4, 2009 and entitled "Electronic Systems for Modeling Chemical Reactions and Biochemical Processes."

BACKGROUND OF THE INVENTION

While chemical reactions involve complex underlying dynamics such as quantum mechanics they can generally be modeled quite well at a higher level using factors such as reactant and product concentration and reaction-rate constants. However, the realistic simulation of chemical reactions and its expansion to the analysis of chemical reaction networks, should include stochastic simulation, because, for example, it is impossible to predict exact molecular population levels through time without considering the kinetic properties of all involved chemical species.

Recent advancements in proteomics and genomics have shed significant light on the individual reactions making up the complex biochemical reaction networks operating in living organisms and these finding would be well complimented by comprehensive and accurate methods for simulating such biochemical networks. However, it is especially important to model stochastics when simulating the biochemical networks, as cells process their mechanical and chemical inputs with highly noisy and imprecise processes that, very often, involve relatively few molecules. Such molecular-dynamics simulations are extremely computationally intensive, especially when the effects of noise, nonlinearity, network-feedback effects, and cell-to-cell variability are included. In spite of efficient stochastic algorithms being available, the computation time of these molecular dynamics simulations increases precipitously when stochastics are included. For example, the most computationally-expensive part of the Gillespie algorithm for simulating chemical reactions is the generation of exponentially-distributed random numbers, which consumes approximately 98% of process time. As a result, the real-time simulation of just 30 state variables with stochastics is quite challenging to implement. The simulation of large-scale reaction networks in cells, which each have up to 30,000 state-variables, is simply beyond the practical limit of traditional computer-based simulation techniques.

One method for reducing the computational expense of simulating reaction networks includes augmenting the digital simulation with a custom analog integrated circuit for generating exponentially-distributed random numbers. This approach is reported to provide a potential speed-up of approximately two orders of magnitude over purely software implementations of the Gillespie algorithm. However, this speed-up is still inadequate for the practical simulation of large-scale reaction networks.

It therefore be desirable the have a system and method for simulating large-scale chemical and biochemical networks that accurately includes stochastics and provides a significant increase in simulation speed over traditional techniques

SUMMARY OF THE INVENTION

The present invention overcomes the aforementioned drawbacks by providing a system and method for simulating chemical and biochemical networks, including their stochastic properties.

In one embodiment, the present invention provides a method for simulating a chemical reaction using an electronic system includes providing an electronic device for modeling a chemical reaction event in which an electron concentration at an input of the electronic device is configured to model a concentration of a reactant in a chemical reaction event, an electron concentration at an output of each exponential current-voltage device is configured to model a concentration of a product in the chemical reaction event, a current flow through the electronic device is configured to model a rate of the chemical reaction event, and a voltage applied at a terminal of the electronic device is configured to model a free energy difference in the chemical reaction event. The method further includes applying a power characteristic at an input of the electronic device, measuring a power characteristic at an output of the electronic device, and generating a report indicative of a chemical species concentration from the measured power characteristic.

In another embodiment, the present invention provides an electronic system for modeling gene expression. The electronic system includes an induction module including at least one exponential current-voltage electronic device and configured to receive an input power characteristic indicative of a simulated concentration of a chemical species and simulate an activation of a transcription factor to produce an output power characteristic indicative of a concentration of the active transcription factor. The system further includes a transcription module including at least one exponential current-voltage electronic device and configured to receive the power characteristic indicative of a concentration of a transcription factor and simulate a genetic transcription process to produce an output power characteristic indicative of mRNA concentration.

In another embodiment, the present invention also provides an electronic system for modeling gene expression that includes an input module configured to receive a power characteristic indicative of a mRNA concentration, a protein dynamics module including at least one exponential current-voltage electronic device and configured to receive the power characteristic indicative of mRNA concentration and simulate a genetic process of translation to produce a power characteristic indicative of a protein concentration, and an output module configured to receive the power characteristic indicative of protein concentration.

In yet another embodiment the present invention provides an electronic system configured to simulate noise in a biochemical reaction network. This electronic system includes a current mode integrator configured to receive an input signal, a current leakage circuit connected to the current mode integrator and configured to produce a leak current, and a control feedback circuit connected to the current leakage circuit and configured to pseudo-randomly control the leak current.

Various other features of the present invention will be made apparent from the following detailed description and the drawings

GENERAL DESCRIPTION OF THE INVENTION

The present invention provides a system for modeling chemical reactions, including large-scale biochemical reaction networks, using "analog" or traditional electronic circuit components and systems. Prior methods for modeling chemical reactions have typically been implemented "digitally" or "virtually" on a computer and, thus, reference to "analog" or "circuit" components should be readily distinguishable from traditional digital models, yet may include electronic components, such as transistors and may be modeled using logic circuits and the like using computer systems.

By exploiting similarities between the equations governing chemical reactions and those governing electronic current flow in certain electronic circuits, the present invention allows large-scale chemical reaction networks to be computed using ultra-fast, highly-parallel analog and hybrid-analog digital circuits that include the effects of molecular stochastics and cell-to-cell variability. Because extracellular cell-cell networks also rely on molecular binding and chemical reactions, the present invention may also efficiently model networks such as hormonal or neuronal networks and simulate cells, tissues, and organs on large-scale electronic chips. In addition, by modifying the electronic simulation circuits, the response of these networks to factors such as pharmaceuticals, pathogens, and gene/protein mutations may be simulated.

There are similarities between chemical reaction dynamics and electronic current flow in electronic devices having exponential current-voltage characteristics where the amount of current flowing through the device is exponentially related to the value of a control voltage applied across one of its terminals. Examples of such "exponential devices" include, for example, transistors such as bipolar junction transistors (BJTs) and metal oxide semiconductor field effect transistors (MOSFETs) operating in a subthreshold regime of operation.

Figure 1:
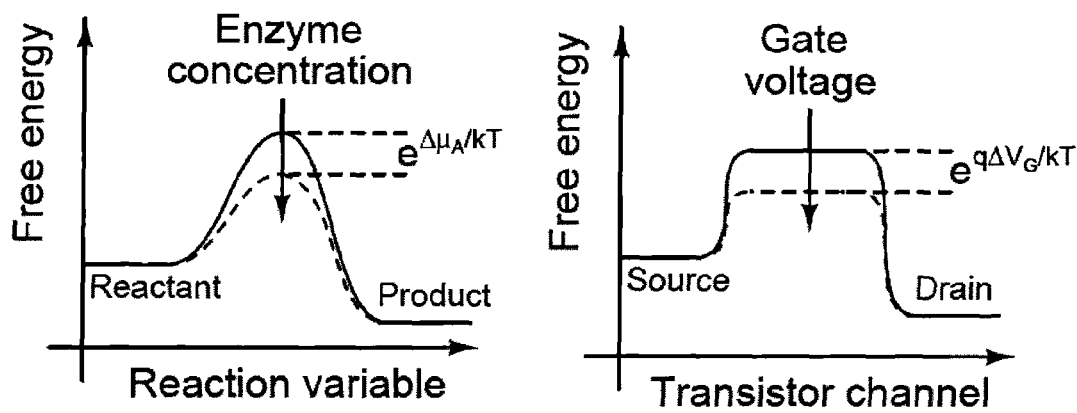
FIG. 1 is a set of graphs comparing chemical reaction dynamics to electron flow in a subthreshold transistor in accordance with the present invention.

For purposes of explanation and with reference to FIG. 1, the discussion will be made with respect to MOSFETs; however, one can readily appreciate that similar analogies can be made in the case of other transistors, such as BJTs. Electron concentrations at the source and drain of MOSFETS are respectively analogous to the concentrations of reactants and products in a chemical reaction, while forward and reverse current flows in the transistor are analogous to forward and reverse chemical reaction rates. Forward and reverse currents in the transistor are exponential in voltage differences at the transistor's terminals. This is analogous to reaction rates being exponential in free energy differences in chemical reactions. Increases in gate voltage lower energy barriers in a transistor and increase current flow. This is analogous to the effects of enzymes or catalysts that increase reaction rates. In addition, the stochastics of Poisson shot noise in subthreshold transistors are analogous to the stochastics of molecular shot noise in reactions. With these analogies or models in place, as will be described, electronic chips may used to mimic and model large-scale chemical-processing systems in biological and artificial networks very efficiently at time scales that are, for example, a million to a billion times faster. In fact, the single-transistor analogy of FIG. 1 can be seen as a good representation, including stochastics, of the chemical reaction $A \rightarrow B$. This automatic inclusion of stochastics is highly beneficial for simulating large-scale chemical reaction networks in an ultra-fast fashion. However, before describing electronic systems for simulating such complicated and expansive reaction networks, voltage-resistor circuits for modeling the differential equations that describe more basic association and dissociation chemical reactions will be described.

An association chemical reaction, for example, that between an enzyme E and a substrate S, may be described by:

$$E + S \underset{k_r}{\overset{k_f}{\rightleftharpoons}} ES;\qquad\text{Eqn. 1}$$

where the enzyme binds to the substrate to create a bound enzyme ES, or $E_b$, via a forward reaction with a reaction-rate constant $k_f$. The product $E_b$ also dissociates via a backward reaction with reaction-rate $k_r$ to recreate E and S. The total amount of enzyme $E_t = E + E_b$ is a constant invariant with time and includes enzyme in both free and bound form. If the concentrations of each enzyme are denoted by brackets around the variable, for example, expressing the concentration of enzyme as [E], and the substrate concentration as [S], then the equations describing the chemical reaction are given by:

$$\frac{d[E_b]}{dt} = k_f[E][S] - k_r[E_b]\qquad\text{Eqn. 2}$$
$$[E] = [E_t] - [E_b].$$

Figure 2A:
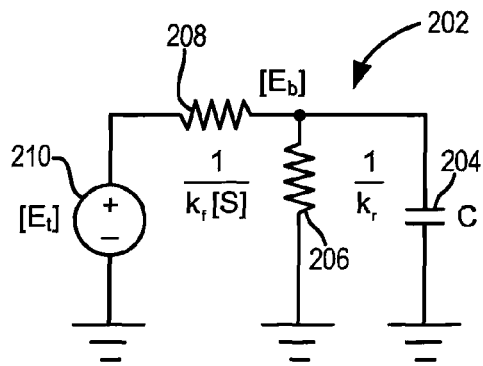
FIGS. 2a and 2b are schematics of electronic circuits for simulating a Michaelis-Menten association reaction and an acid dissociation reaction in accordance with the present invention.

Referring now to FIG. 2a, and assuming that [S] is constant, this association reaction can be modeled using a circuit 202 having a capacitor 204 having a capacitance C in parallel with a resistor 206 having a resistance $1/k_r$ and another resistor 208 having a capacitance $1/(k_f[S])$ in series with a voltage source 210 having a value $[E_t]$. If C=1, then currents through the resistors 206 and 208 represent the forward and backward fluxes of the chemical reaction of Eqn. 1. At equilibrium, when the voltage of the capacitor 204 has reached a constant value, the two currents are equal and the circuit 202 functions like a resistive-divider. Using resistive-divider analysis it can therefore be shown that:

$$[E_b] = [E_t]\left(\frac{[S]/K_d}{[S]/K_d + 1}\right)\qquad\text{Eqn. 3}$$
$$K_d = \frac{k_r}{k_f}$$
$$K_a = \frac{k_f}{k_r} = \frac{1}{k_d}.$$

Thus, when [S] is significantly greater than $K_d$, the enzyme substrate binding is said to exhibit saturation, since the fraction of bound enzyme is limited by the total enzyme concentration $[E_t]$ rather than by the substrate concentration [S]. The resistive-divider network 202 reveals that circuit analogies allow rapid understanding of Michaelis-Menten kinetics of enzyme-substrate binding or of other association reactions. In many biological systems, $[E_b]$ leads to slower production of a product P at a flux rate of $v[Eb]$ via a further unidirectional reaction accompanied by unbinding of the enzyme and substrate. This reaction may be represented by including a resistance value of $1/v$ in parallel with the resistor 206 of the resistive-divider network 202. In addition, a voltage-dependent transconductance having an output current depending on $[E_b]$, as $v[E_b]$ charges a capacitance $C_2=1$, may also be employed so that the voltage of the capacitor 204 represents the concentration of P. While, simple circuit blocks can represent biochemically realistic enzyme kinetics more exactly if needed, the central dynamics of Michaelis-Menten kinietics are well represented by Eqns. 2 and 3 and the resistive-divider network 202.

Figure 2B:
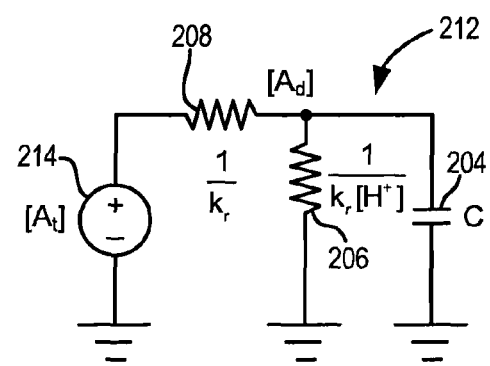

Referring to FIG. 2b, by employing the above-described principles, a dissociation reaction, for example, that due to an acid, can be given by:

$$HA \underset{k_r}{\overset{k_f}{\rightleftharpoons}} H^+ + A^-;\qquad\text{Eqn. 4}$$

and represented using the circuit 212 where a voltage source 214 having a value $[A_t]$ is the amount of acid in total form, that is, undissociated as HA, or dissociated as $[A^-]=[A_d]$ so that $[A_t]=[HA]+[A_d]$.

Figure 3:
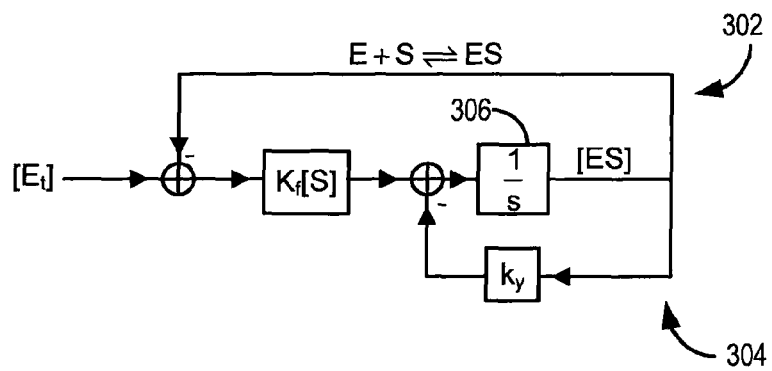
FIG. 3 is a schematic of two feedback loops that can be seen to occur during a chemical reaction.

Referring particularly to FIG. 3, chemical reactions, including the enzyme-substrate binding reaction of Eqn. 1, can be modeled as a system that includes two negative-feedback loops. First, a primary feedback loop 302 arises because the concentration of reactants falls as the concentration of product builds, thus slowing the forward reaction. A secondary feedback loop 304 arises because the backwards reaction speeds up when the concentration of the products builds. At steady-state, the 1/s integrator 306 has infinite gain such that the feedback path of the secondary loop 304 determines the closed-loop transfer function of the secondary loop 304. Therefore, the feedback loop also leads to Michaelis-Menten saturation, except that the saturation can be viewed as a high-loop-gain effect with loop-gain $[S]/K_d$. The primary loop 302 can be seen to correspond to the discharging current through the resistance $1/k_f$ in the circuit 202, while the secondary loop 304 can be send to correspond to the charging current through the resistance $1/k_r$.

One set of differences between chemical resistive-divider circuits and electronic resistive-divider circuits lie in their respective noise properties. The current in real resistors flows by drift, while their 4kTR current noise per unit bandwidth is due to the shot noise of internal diffusion currents. In contrast, the resistor current and resistor noise currents of FIGS. 2a and 2b are both due to diffusion currents that exhibit Poisson noise statistics, that is, the resistors noise is the shot noise of the current flowing through it and it varies with current flow. Therefore, the exponential device analogy of FIG. 1 is more accurate than the resistor analogy of FIGS. 2a and 2b, as it correctly simulates both current and noise for a given reaction. This is an important consideration for biochemical reactions, as cells process their mechanical and chemical input signals with highly noisy and imprecise parts. Nevertheless, if the correct shot-noise formulas pertaining to the resistors of the circuit 202 are employed, it is possible to compute the total concentration noise on the capacitor 204. The shot noise on the currents flowing through the resistors 206 and 208 is converted to voltage noise on the capacitor 204, as in a simple RC circuit having two resistors in parallel. To analyze mass currents rather than charge currents, the following conditions may be set:

$$q=1$$
$$C=\text{Volume}\qquad\text{Eqn. 5}$$

Assuming that [S] is nearly constant and exhibits no noise, for example, because [S] is large, then provides:

$$k'_f = k_f[S] \quad \text{Eqn. 6}$$

$$\overline{v_n^2} = 2q\left(E_t\left(1 - \frac{k'_f}{k'_f + k_r}\right)k'_f + E_t\left(\frac{k'_f}{k'_f + k_r}\right)k_r\right) \times$$

$$\frac{1}{(k'_f + k_r)^2} \times \frac{k'_f + k_r}{2\pi C} \times \frac{\pi}{2}$$

$$\overline{v_n^2} = 4qE_t\left(\frac{k'_f k_r}{k'_f + k_r}\right)\frac{1}{(k'_f + k_r)} \times \frac{1}{4C}$$

$$= \frac{E_t}{C}\frac{k'_f k_r}{(k'_f + k_r)^2}$$

$$\overline{v_n^2} = \frac{E_t}{C}\left(\frac{k'_f}{(k'_f + k_r)}\right)\left(\frac{k_r}{(k'_f + k_r)}\right).$$

The result of Eqn. 6 has the 1/C scaling expected from the kT/C relationship for noise on the capacitor 204. Computing total fluctuation in the number of bound enzyme molecules $\sigma_N$ on the capacitor C 204 provides:

$$\sqrt{\sigma_N^2} = \sqrt{\frac{E_t}{C}\left(\frac{k'_f}{(k'_f + k_r)}\right)\left(\frac{k_r}{(k'_f + k_r)}\right)}\, C \quad \text{Eqn. 7}$$

$$\sigma_N = \sqrt{E_t C\left(\frac{k'_f}{(k'_f + k_r)}\right)\left(\frac{k_r}{(k'_f + k_r)}\right)}$$

$$\sigma_N = \sqrt{Np(1-p)}\,;$$

where $N_t = E_t C$ is the total number of enzyme molecules, bound or unbound, within a volume compartment C of the reaction and p is the probability that an enzyme is bound. Noise is therefore maximized when the probability of an enzyme molecule being bound is ½ and is minimized when the probability is near 1 or 0. Intuitively, a chemical reaction having a forward flux greatly in excess of the reverse flux, that is, p=1, will exhibit little noise since almost all molecules will be bound. Likewise, a chemical reaction where p=0 will exhibit little noise as almost all the molecules will be unbound. This is similar to transport channels in a cell membrane, which exhibit the least noise when the probability of opening is near 1 or 0.

More generally, the dynamics of a chemical species i with concentration $x_i$ in a chemical reaction can be described by a differential equation of the form:

$$\frac{dx_i}{dt} = \sum_j c_j + \Sigma_l k_{il} u_l + \Sigma_m k_{im} x_m + \Sigma_{lm} k_{ilm} x_l x_m + \Sigma_{np} k_{inp} x_n u_p + \ldots\,; \quad \text{Eqn. 8}$$

where various externally controlled input species u(t) and state-variable chemical species x(t) undergo zeroth order interactions ($c_j$ terms), first order interactions ($k_{il}$ and $k_{im}$ terms), second order interactions ($k_{ilm}$ and $k_{inp}$ terms), or higher-order interactions to create fluxes that increase $x_i$ (positive kinetic rate constants k) or decrease $x_i$ (negative kinetic rate constants k). In almost all chemical reactions at practical temperatures, pressures, and concentrations, the reaction dynamics of all involved species can be sufficiently described using the zeroth, first, and second order terms of Eqn. 8. Higher-order terms due to the simultaneous association or dissociation of more than two chemical species have a vanishingly low probability and most reactions that involve the association or dissociation of more than two species usually occur via chemical intermediates with, at most, two species associating or dissociating at any given time. Thus, Eqn. 8 can be truncated after the second-order terms and still provides an excellent description of reaction dynamics. These equations can be written for every state-variable species i involved in the reaction and the reaction outputs $y_i(t)$ can be considered as a linear combination of the input species such that:

$$y_i = \Sigma_j r_{ij} x_j + \Sigma_j s_{ij} u_j \quad \text{Eqn. 9}$$

Thus, chemical reactions can typically be described using polynomial nonlinear differential equations with an order of two. Translinear circuits are capable of creating both linear and nonlinear static and dynamic systems through the use of exponential nonlinear devices. Given the similarities between chemical computation and electronic computation, as outlined with reference to FIG. 1, log-domain bipolar and subthreshold circuits with exponential nonlinearities can be employed to model the dynamics of chemical reaction networks. While this can be performed for polynomial nonlinear dynamical networks of any order, the present invention is described with respect to second order systems because they satisfactorily characterize most chemical reactions.

To map chemical reaction networks to current-mode circuits, appropriate amplitude and time constant scaling from the chemical to the electrical domain may be selected. For instance, amplitude scaling can be accomplished by setting:

$$\frac{x_i}{X_0} = \frac{i_i}{I_i}. \quad \text{Eqn. 10}$$

This equation states that the normalized concentration of a chemical concentration $x_i$ with respect to a global reference concentration $X_0$ is equal to a normalized current $i_i$ with respect to a global reference current $I_0$. To allow the normalized electrical state variable $i_i/I_0$ to have a time derivative that is a times faster than the normalized chemical state variable $x_i/X_0$, the kinetic rate constants in the chemical equation can be replaced by equivalent electrical rate constants. A kinetic term in a chemical differential equation will therefore scale according to:

$$\frac{dx_i}{dt} = \ldots + \Sigma_{lm} k_{ilm} x_l x_m + \ldots \quad \text{Eqn. 11}$$

$$X_0 \frac{d(x_i/X_0)}{dt} = \ldots + X_0^2 \Sigma_{lm} k_{ilm} \frac{x_l}{X_0}\frac{x_m}{X_0} + \ldots$$

$$X_0 \frac{1}{\alpha}\frac{d(i_i/I_0)}{dt} = \ldots + X_0^2 \Sigma_{lm} k_{ilm} \frac{i_l}{I_0}\frac{I_m}{I_0} + \ldots$$

$$\frac{d(i_i/I_0)}{dt} = \ldots + \Sigma_{lm}(\alpha X_0^1 k_{ilm})\frac{i_l}{I_0}\frac{I_m}{I_0} + \ldots\,.$$

This provides a kinetic rate that transforms according to:

$$k \rightarrow \alpha X_0^{(S-1)} k \quad \text{Eqn. 12;}$$

where S is the order of a given term in the chemical equation, for example, zeroth/first/second-order, when mapping from the chemical domain to the electrical domain. It should be noted that the scaling of Eqn. 12 also applies to the input terms u in the chemical equation, which can also be normalized by $X_0$. The last row of Eqn. 11 can be transformed into a form suitable for a log-domain dynamical system by multiplying the left and right hand sides by the reciprocal of $i_i/I_0$ to provide:

$$\frac{1}{(i_i/I_0)} \frac{d(i_i/I_0)}{dt} = \ldots + \Sigma_{lm} k_{ilm} \frac{\frac{i_l}{I_0} \frac{I_m}{I_0}}{(i_i/I_0)} + \ldots \qquad \text{Eqn. 13}$$

$$\frac{C_i \frac{\varphi_t}{\kappa}}{i_i} \frac{di_i}{dt} = \ldots + I_0 \Sigma_{lm} \left( \alpha \frac{C_i \frac{\varphi_t}{\kappa}}{I_0} X_0^1 k_{ilm} \right) \frac{\frac{i_l}{I_0} \frac{I_m}{I_0}}{(i_i/I_0)} + \ldots$$

$$C \frac{dv_{Ci}}{dt} = \ldots + I_0 \Sigma_{lm} (\beta_{ilm}) \frac{\frac{i_l}{I_0} \frac{I_m}{I_0}}{(i_i/I_0)} + \ldots$$

$$\beta_{ilm} = \alpha \frac{C_i \frac{\varphi_t}{\kappa}}{I_0} X_0^1 k_{ilm}$$

$$\beta_{ilm} = \alpha \tau_{0i} X_0^1 k_{ilm};$$

where $v_{Ci}$ is the log-domain voltage on capacitor $C_i$ that represents $\log(x_i/X_0)$ as $(\phi_t/\kappa)\ln(i_i/I_0)$, with $(\phi_t/\kappa)$ being the characteristic subthreshold exponential voltage ($\kappa=1$ in the case of a biopolar transistor) and $\tau_{0i}=C_i(\phi_t/\kappa)/I_0$ being a characteristic electrical time constant. Performing a similar transformation for the terms of other orders gives:

$$\frac{dx_i}{dt} = \ldots + \Sigma_m k_{im} x_m + \Sigma_{lm} k_{ilm} x_l x_m \Sigma_{np} k_{inp} x_n u_p \qquad \text{Eqn. 14}$$

$$C_i \frac{dv_i}{dt} = I_0 \bigg( \ldots + \Sigma_m \beta_{im} \frac{i_m/I_0}{i_i/I_0} + $$

$$\Sigma_{lm} \beta_{ilm} \frac{(i_i/I_0)(i_m/I_0)}{i_i/I_0} + \Sigma_{np} \beta_{inp} \frac{(i_n/I_0)(u_p.I_0)}{i_i/I_0} + \ldots \bigg);$$

where the dimensionless kinetic rate constants $\beta_i$ in the electrical system are related to corresponding constants in the chemical domain by:

$$\beta_{i\ldots} = (\alpha \tau_{0i} X_0^{S-1}) k_{i\ldots} \qquad \text{Eqn. 15;}$$

where $S=[0, 1, 2]$ for the zeroth, first, and second order terms respectively. While Eqns. 14 and 15 describe transformations for a particular chemical species i, an identical transformation can applies to all other species involved in the dynamics. This allows the chemical potential of a given state variable $x_i$ to be mapped to a capacitor $C_i$. Therefore, if an original chemical dynamical system has N state variables, M inputs, and P outputs, then the analogous electronic system includes N capacitors, M current inputs, and P current outputs.

More formally, a reaction system including N species x, M inputs u, and P outputs y with zeroth, first, and second-order mass-action kinetics can be considered. To model forward and backward reactions through separate unidirectional differential equations, such a system can be described as follows:

$$\frac{dx}{dt} = C + Dx + E(x \otimes x) + Fu + G(x \otimes x) \qquad \text{Eqn. 16}$$

$$y = Hx + Ku;$$

where $\otimes$ denotes the outer product of the two vectors. While Eqn. 16 appears similar to the standard state-space equations of linear control theory, the inclusion of the $x \otimes x$ term adds polynomial nonlinearities that are not present in the standard linear equations of control theory. The reaction system of Eqn. 16 can be simulated by storing the chemical potential of a species, that is, the Gibbs free energy per molecule, as the voltage V on a capacitor of value C. In dilute solutions, the chemical potential of the i-th species may be given by:

$$\mu_i = \mu_0 + k_B T \ln\left(\frac{x_i}{X_0}\right); \qquad \text{Eqn. 17}$$

where $\mu_0$ and $X_0$ are constants respectively referred to as the reference chemical potential and reference concentration and $x_i$ is the concentration of the species. It should be noted that $\mu_0$ and $X_0$ can be assumed to be the same for all species. When this assumption is implicit, it can be shown that Eqn. 17 can be used to derive a number of well-known colligative laws, such as the ideal gas law, law mass action, Raoult's law, Henry's law, Nernst's distribution law, and the osmotic pressure law. As such, Eqn. 17 may conceptually be treated as a basic law.

For non-dilute solutions and/or charged species, Eqn. 17 can typically be applied by replacing $x_i$ with an effective concentration $x_i a_i$, where $a_i$ is the activity coefficient of a given species. By dividing by $\kappa q$, where $\kappa$ is a constant and q is an electronic charge, it is possible to convert from $\mu$ to V. Eqn. 17 can then be expressed as:

$$\ln\left(\frac{x_i}{X_0}\right) = \frac{\kappa(v_i - V_0)}{\phi_T} \Rightarrow x_i = X_0 \left(\frac{\kappa(v_i - V_0)}{\phi_T}\right); \qquad \text{Eqn. 18}$$

where $\phi_T = k_B T/q$ is the thermal voltage and $V_0 = \mu_0/(\kappa q)$ is a constant reference voltage. Concentrations of input and output species can be encoded similarly. Differentiating both side of Eqn. 18 provides:

$$\frac{d\ln(x_i)}{dt} = \frac{1}{x_i} \frac{dx_i}{dt} = \frac{\kappa}{\phi_T} \left(\frac{dv_i}{dt}\right). \qquad \text{Eqn. 19}$$

For convenience, these concentrations can be converted using the reference current $I_0$ and reference voltage $X_0$ so that $i_i/I_0 = x_i/X_0$ and $i_i = I_0 \exp(\kappa(v_i - V_0)/\phi_T)$. Similarly, $i_{ui}/I_0 = u_i/X_0$ and $i_{yi}/I_0 = y_i/X_0$ may also be defined. Thus, Eqns. 16 and 19 together provide:

$$C \frac{dv_i}{dt} = \frac{C\phi_T}{\kappa I_0} \Bigg[ \frac{c_i}{X_0} \frac{I_0^2}{i_i} + \sum_{j=1}^{N} d_{ij} \frac{I_0 i_j}{i_i} + \qquad \text{Eqn. 20}$$

$$X_0 \sum_{j=1}^{N} \sum_{k=1}^{N} e_{ijk} \frac{i_j i_k}{i_i} + \sum_{j=1}^{M} f_{ij} \frac{I_0 i_{uj}}{i_i} + X_0 \sum_{j=1}^{N} \sum_{k=1}^{M} g_{ijk} \frac{i_j i_{uk}}{i_i} \Bigg];$$

and $$i_{yi} = \sum_{j=1}^{N} h_{ij} i_j + \sum_{j=1}^{M} k_{ij} i_{uj}. \qquad \text{Eqn. 21}$$

These equations are statements of Kirchoff's Current Law (KCL), where index i runs from 1 to N in the first equation and 1 to P in the second equation, corresponding to N state variables and P outputs, respectively. The reference concentration $X_0$ and the reference current $I_0$ are generally chosen to be geometric means of the minimum and maximum concentrations and currents of interest. It is contemplated that, in subthreshold CMOS implementations, the minimal allowable current may be set by leakage and parasitic capacitances, while the maximum is set by the onset of strong inversion. Eqns. 20 and 21 are dynamically equivalent to the original chemical equations, that is, the dynamics of normalized chemical and electrical variables, such as $i_i/I_0$ and $x_i/X_0$, are identical.

Eqn. 20 can be implemented in hardware using log-domain circuits, in which the currents $i_i$ are proportional to $\exp(\kappa v_i/\phi_T)$, where $i_i \geq 0$, $\forall i$. Thus, each current can be created by a single BJT operating in its forward active region or subthreshold MOSFET operating in its saturated region. Further, many chemical reaction networks are sparse and most species participate in fewer than four reactions. This sparseness implies that most of the coefficients, for example, $c_i$, $d_{ij}$, $e_{ijk}$, $f_{ij}$, and $g_{ijk}$ are zero, as the reactions in question do not occur. Therefore, only a small subset of the $1+N+N^2+M+MN$ terms on the right hand side of Eqn. 20 are non-zero and each of these contributes a current $\pm \beta_1 i_2/i_i$ to $Cdv_i/dt$, where $\beta$ is a dimensionless, non-negative constant and $i_1$ and $i_2$ are non-negative currents. As a result, Eqn. 20 can be implemented with single-quadrant log-domain integrators, which themselves can be implemented using very few transistors, and Eqn. 21 can be implemented in a similar manner. The N state variable currents $i_j$ and M input currents $i_{uj}$ can be summed together at a single node with appropriate weighting factors $h_{ij}$ and $k_{ij}$, thereby resulting in an output current $i_{yi}$. P such summations can be performed to produce P output currents.

Reaction networks should satisfy the thermodynamic constraint that the net change in thermodynamic potential around any reaction loop is zero. For biochemical reaction networks the appropriate potential is usually the Gibbs free energy G. This statement is an application of the first law of thermodynamics, which states that total energy is conserved, and can be expressed mathematically as:

$$\sum_{j \in loop} (\mu_j - \mu_{j,eq}) = 0 \Rightarrow \sum_{j \in loop} (v_j - v_{j,eq}) = 0; \quad \text{Eqn. 22}$$

where the second equation follows from the first by employing Eqns. 17 and 18, and wherein $\mu_{j,eq}$ is the chemical potential of the j-th chemical species at thermodynamic equilibrium. It should by noted that the second equation corresponds to a version of Kirchoff's voltage law (KVL). Accordingly, a circuit model in accordance with the present invention may incorporate thermodynamic constraints, though it should be noted that the model does not necessarily model changes in reaction rates with temperature accurately, since activation energies can depend on temperature in complicated ways. This occurs because molecules can have several internal degrees of freedom that affect their interactions. For example, diatomic molecules can rotate about the bond linking the two atoms and this process has its own characteristic dependence on temperature. It should be noted that analogous phenomena occur in electronics, because the threshold voltage of a transistor is typically a complicated function of temperature. However, as shown in FIG. 1, at a given temperature, flux in both chemical and electronic systems is proportional to $\exp(-E/kT)$, where E is the height of the energy barrier, such as activation energy or threshold voltage, that controls the flow. Thus, the electronic circuits reproduce the well-known Arrhenius relationship between chemical reaction rates and absolute temperature.

The total potential energy of charged molecules is determined both by chemical and electrostatic potentials. Their combined effects can be expressed via the electrochemical potential, which is defined as $$\mu_{ec} = \mu_c + zqN_A V \quad \text{Eqn. 23;}$$

where $\mu_c$ is the chemical potential, zq is the charge on the ion, $N_A$ is Avogadro's number, and V is the voltage, or electrostatic potential. Since $\mu_{ec}$ changes linearly with V, one can use voltage to exponentially speed up or slow down the rates of reactions that involve the loss or gain of electrons, such as redox reactions. Such effects can be modeled by individually programming the rate constants of forward and reverse reactions. In addition, voltage gradients, that is, electric fields, cause gradients in $\mu_{ec}$ that cause ions to flow via drift, though such gradients are absent in homogenous media and, as a result, fluxes in well-mixed, homogenous media are purely diffusive in nature.

Figure 4:
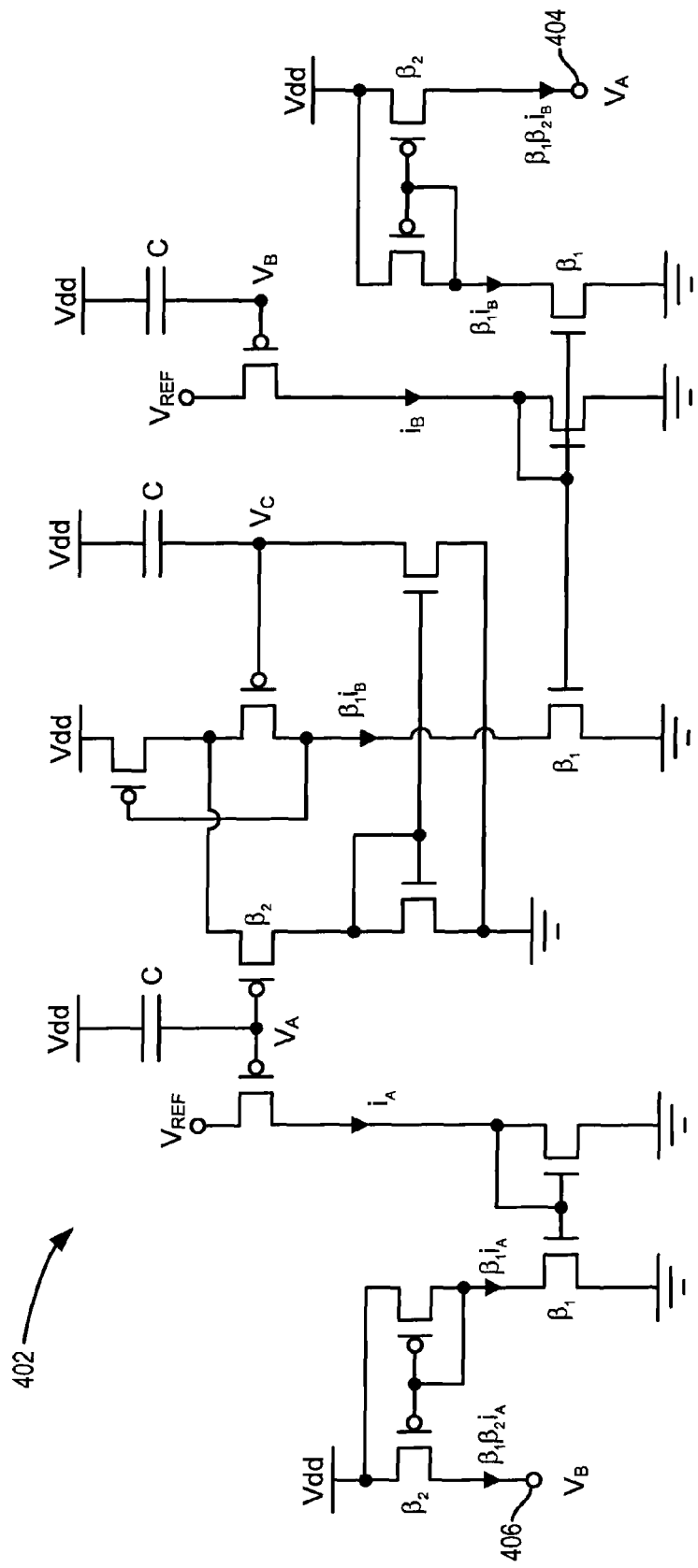
FIG. 4 is a schematic of a second-order, log-domain chemical reaction circuit for modeling a unidirectional reaction in accordance with the present invention.

Referring now to FIG. 4, as an example, a log-domain circuit 402 may be employed to implement the differential equations that model the second-order unidirectional equation A+B→C. In the log-domain circuit 402, to model the second-order unidirectional equation A+B→C, A is represented as a voltage source 404 having a value $V_A$ that is applied to the circuit 402 and B is represented as a voltage source 406 having a value $V_B$ it is applied as a second input of the circuit 402. An analysis of the circuit 402 yields the following differential equations:

$$\beta = \beta_1 \beta_2 \quad \text{Eqn. 24}$$

$$C\frac{dv_C}{dt} = -\beta \frac{i_A i_B}{i_C}$$

$$C\frac{dv_B}{dt} = +\beta \frac{i_A i_B}{i_B} = +\beta i_A$$

$$C\frac{dv_A}{dt} = +\beta \frac{i_A i_B}{i_A} = +\beta i_B.$$

It should be noted that the signs of the current are reversed because the state variable $v_i$ is referenced to $V_{DD}$ and is therefore given by $(V_{DD}-v_i)$. The parameters $\beta_1$ and $\beta_2$ are altered by DAC-programmable bias currents with $\beta=\beta_1\beta_2$, thus providing a large dynamic-range if programmability in $\beta$ with two lower dynamic-range DACs. Using the log-domain circuit 402, the concentrations of $I_A$ and $I_B$ may be kept constant by holding the voltage of nodes $V_A$ and $V_B$.

The backward reaction C→A+B can be implemented using a similar circuit, where the backward-reaction $\beta_r$ is varied relative to the forward-reaction $\beta_f$ to vary $K_d=(I_0 \beta_r/\beta_f)$. In normal non-log-voltage units, the overall current-mode circuit then simulates a constant forward-reaction current source that exhibits Poisson noise statistics and is connected to a conductance proportional to $K_d$, which is in parallel with a capacitance and the current source. In this case, the voltage on the capacitance represents the concentration of the chemical species C and, due to the reverse current flowing through it, the conductance proportional to $K_d$ exhibits Poisson statistics as well. In effect, this provides a parallel RC circuit fed by a current source with shot noise from the current source and shot noise from the current flowing through the R. It should be noted that the power spectral density (PSD) of the current through R is not 4kTG. If the forward-reaction current source has a value of I, then the voltage $v_C$ equilibrates at a value such that it is balanced by the backward-reaction current through R. Thus, the noise voltage on the capacitor C may be given by:

$$\overline{v_n^2} = (2qI + 2qI)(R^2)\left(\frac{\pi}{2}\right)\left(\frac{1}{(2\pi)RC}\right) = \frac{q(IR)}{C};\qquad \text{Eqn. 25}$$

where signal-voltage power on the capacitor is given by:

$$v_C^2 = (IR)^2 \qquad \text{Eqn. 26}$$

and the net signal-to-noise ratio (SNR) of the circuit is given by:

$$SNR = \frac{v_c^2}{\overline{v_n^2}} = \frac{C(IR)}{q}.\qquad \text{Eqn. 27}$$

In an actual current-mode circuit, IR is represented by an equivalent output current $I_C$, such that Eqn. 27 predicts that the SNR of the current-mode circuit increases as the mean value of $I_C$ increases and is dependent on the net value of $I_C$, rather than the value of R or $K_d$. These predictions can be confirmed when noise simulations are performed on a bi-directional current-mode equivalent circuit. The simulations indicate that the stochastics of the current-mode circuit do indeed represent those seen in chemical reactions. Further, it can be shown that saturation at large SNRs is primarily due to flicker noise and that the value of C can be used to scale the SNR. At very low SNRs, for example, those below 20 dB, parasitic capacitances and leakage currents limit the reliable control of SNR in the circuit. In these situations, a noise generation circuit, which will be described later, can be employed to reliably add artificial noise with the correct Poisson properties to a quiet electronic circuit.

Mismatches between transistors used to carry chemical fluxes can be problematic when modeling some chemical reactions. For example, the unidirectional reaction A→B having a reaction rate constant k conserves the total amount of A and B, since d([A]+[B])/dt=−k[A]+k[A]=0. The conserved quantity arises from the fact that the creation of a molecule of B involves the destruction of molecule of A. However, when this reaction is simulated electronically the current leaving the node representing [A] is generally not precisely equal to the current entering the node representing [B]. This occurs because of mismatch and is difficult to avoid in any real electronic circuit. One way to completely avoid mismatch is to use the same transistor, or other two-terminal device, to shuttle charge between the two nodes. However, this is not possible in a variety of situations. It is therefore contemplated that mismatches may be reduced by employing other measures. Passive mismatch reduction techniques, which do not necessitate changes to overall circuits, include using transistors that are physically larger and are positioned closer to each other on a die. Active mismatch reduction techniques include the use of fully-differential circuit topologies and dynamic matching schemes in which the circuit uses one array of transistors at any given time and rapidly switches between them. Mismatch can be removed in hardware by periodically auto-zeroing output buffers to cancel the offset voltage of a closed-loop amplifier. This can be achieved by sampling the offset on a capacitor $C_{AZ}$ during an auto-zero phase and removing the offset during an operating phase by connecting $C_{AZ}$ to the negative input terminal of the amplifier. Buffers may be auto-zeroed in this way by using the periods between simulation runs as auto-zero phases. Auto-zeroing is an example of a more general technique known as correlated double sampling. It is further contemplated that other correlated double sampling techniques can also be employed to reduce mismatches or offsets between translinear circuits used for modeling chemical reaction networks.

It should be noted that the above-described models and electronic systems, as well as those that follow, can be employed to simulate reaction systems having either a single compartment or multiple compartments, whether well-mixed or spatial heterogeneous. A single compartment has a constant volume for all species and thereby allows mass-action rate laws to be written in terms of concentration as (mass/volume), because the volume is a scalar. More general multi-compartment models can be modeled by assuming that all reactants participating in a given reaction are present in the same compartment. This is beneficial, because, multi-compartment models are common in biology. In cell-signaling pathways, for example, the extra-cellular environment, cell membrane, cytoplasm, and nucleus may be considered as separate, well-mixed compartments. As another example, drug delivery may also be considered as a set of well-mixed compartments. Systems that are not well-mixed generally exhibit spatial gradients in concentration that cause mass transport due to diffusion. These systems can be modeled using the present invention by spatially discretizing the system into chambers small enough to be approximated as well-mixed at timescales of interest. For example, spatial variations in the concentrations of chemical species simulated in this way and stored on a set of capacitors.

While the present invention can be employed to model general chemical reactions as outlined above, its use in modeling the extensive biochemical networks and biological processes present in living organisms is particularly useful. Cells in the human body provide examples of phenomenally energy-efficient sensing, actuation, and processing operations. An average human cell, which is approximately 10 μm in size, hydrolyzes energy-carrying adenosine-tri-phosphate (ATP) molecules to perform nearly $10^7$ ATP-dependent biochemical operations per second. Since, under the conditions in the body, the hydrolysis of one ATP molecule provides about 20 kT, or $8\times10^{-20}$ J, of metabolic energy, the net power consumption of a single human cell is an astoundingly low 0.8 pW. The nearly 100 trillion cells of the human body thus have an average resting power consumption of about 80 W. Cells process their mechanical and chemical input signals with highly noisy and imprecise parts. Nevertheless, cells perform complex, highly sensitive, and collectively precise hybrid analog-digital signal processing on their inputs such that reliable outputs are produced. Such signal processing enables a cell to sense and amplify minute changes in the concentrations of specific molecules amidst a background of confoundingly similar molecules, harvest and metabolize energy contained in molecules in its environment, detoxify and/or eject poisonous molecules, sense its infection by a virus; and communicate with other cells. The signal processing also allows the cell to move, maintain its structure, regulate its growth in response to signals in its surround, speed up chemical reactions via sophisticated enzymes, and replicate itself when appropriate. Because different chemical reactions and their stochastic properties can be efficiently and programmably represented by groups of subthreshold or bipolar transistors in an analog circuit, the approximately 30,000 gene-protein and protein-protein reaction networks that implement and regulate these cellular functions can be modeled using the present invention.

An inducer molecule, for example, glucose, may enter a cell and cause biochemical reaction events via a protein-protein network that lead to the activation of a particular protein known as a transcription factor. The activation of the transcription factor most often occurs because a molecule binds to the transcription factor and changes its shape, thereby allowing it to bind with DNA near or within specific promoter binding sites that have a particular nucleotide sequence. The binding of the transcription factor causes the transcription rate of a gene near the promoter to be increased if the transcription factor is an activator or decreased if it is a repressor. Transcription is the process in which the enzyme RNA-polymerase coverts the DNA sequence of a gene into a corresponding messenger RNA (mRNA) that may then be translated by a ribosome into a sequence of corresponding amino acids to form a protein. The final translated protein can act as a transcription factor for other genes in a gene-protein network or affect other proteins in a protein network or do both. The translated protein can also serve as an activator or repressor for its own gene.

In addition to general chemical reaction dynamics, gene-protein networks are known to incorporate logic-like operations. For example, when E. Coli are cultured in a medium that lacks glucose but has lactose, the bacteria increase the transcription rate of certain genes that are normally expressed at a very low level. These genes produce proteins that help metabolize lactose to obtain energy, transport lactose into the cell, and detoxify toxic metabolites caused by lactose metabolism. If glucose is present, these genes are not expressed, as it is significantly 'cheaper' for the cell to metabolize glucose rather than lactose if possible. Therefore, the bacteria do not bother making proteins useful for lactose metabolism if glucose is present and the cell effectively behaves as though the expression of these genes is based on the logical expression NOT(Glucose) AND Lactose.

Figure 5:
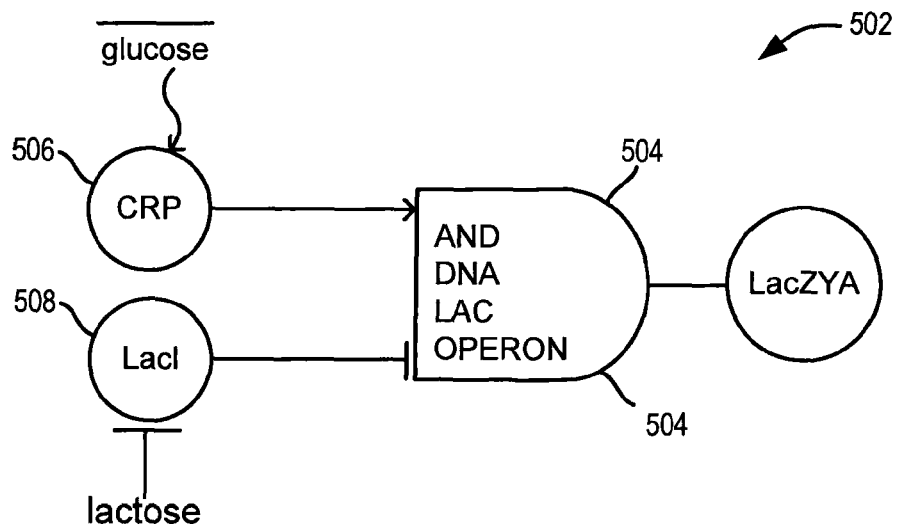
FIG. 5 shows a logic circuit for the activation of lactose metabolism in E. Coli.

Referring to FIG. 5, experiments have shown that the absence of glucose induces an activator transcription factor called CRP to become active and bind DNA in an enhancer region of the DNA. Its binding enhances the transcription rate of RNA polymerase in a catalytic fashion by helping 'recruit' RNA polymerase to bind near the enhancer and thus begin transcription of genes near the enhancer region. The presence of lactose induces a repressor transcription factor called LacI to become inactive and unbind from DNA in a promoter region of the DNA adjacent to the enhancer region where CRP binds. RNA polymerase must bind to DNA in this promoter region for transcription of nearby genes to begin. Thus, the unbinding of LacI serves to unblock the binding of RNA polymerase on the promoter and consequently enables transcription to proceed. Thus, the interactions between the transcription factors on DNA is analogous to the manner in which multiple inputs affect the output of a logic gate as indicated generally at 502. The 'AND DNA Lac operon' 504 increases the transcription of the sequentially adjacent LacZ, LacY, and LacA genes, if the CRP activator 506 is bound and the LacI repressor 508 is unbound. These sequentially adjacent genes are said to be on a common operon whose transcription is controlled by the binding and unbinding of the CRP and LacI transcription factors to the enhancer and promoter DNA regions respectively, both of which are near each other and near the Lac genes. In general, interactions between transcription factors can lead to multiple-input 'logic functions', though it should be noted that the true interactions are not digital, but analog.

Figure 6:
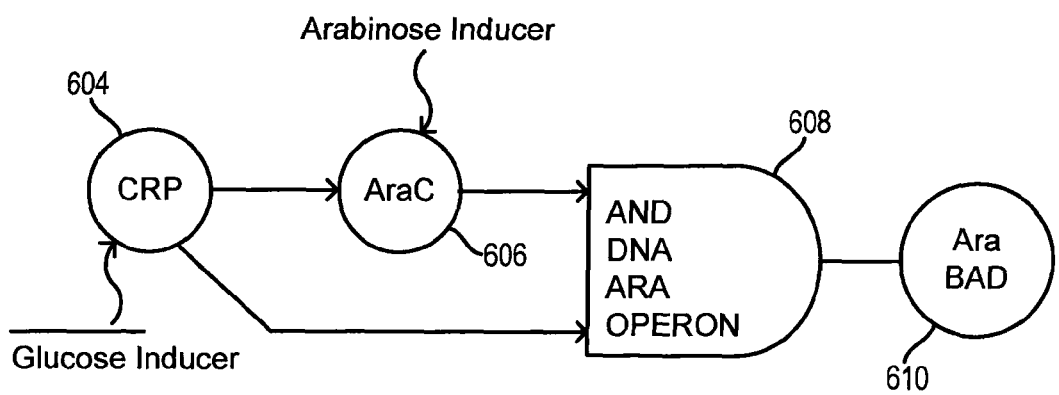
FIG. 6 shows a logic circuit for the activation of arabinose metabolism in E. Coli.

In many molecular circuits in bacteria and yeast, delays in transcription and translation are relatively negligible compared to mRNA or protein degradation time constants and can be approximated by adding slight increases to the time constants. However, in mammalian cells, the delayed transcription of relatively long genes can take upwards of 30 minutes and may exceed the mRNA degradation time, which generally ranges from 10 minutes to 10 hours. Accordingly, it can be important to represent these delays in electronic models of biochemical reaction networks Referring to FIG. 6, as an example of time-varying reaction conditions, a feed-forward logic (FFL) circuit common in E. Coli bacteria and other cells is indicated generally at 602. When activated, the output genes of this circuit produce proteins useful for metabolizing and processing arabinose, a sugar. This circuit, which implements NOT (glucose) AND (arabinose), may be compared with that of FIG. 5, which implements NOT (glucose) AND lactose. While both circuits have similar functions, there are significant differences in their topologies that lead to differences in how they process their respective inputs. The CRP transcription factor 604 and AraC transcription factor 606 that are activated by the respective absences of glucose and arabinose are in series. As a result, AraC production begins only if the CRP protein 604, which is activated by the presence of glucose, activates the transcription of genes that produce AraC, whose activation is induced by the presence of arabinose. Therefore, the combination of an active CRP and an active AraC leads to the production of the AraBAD proteins 610 via the "AND DNA Ara operon" 608. While the logic of FFL circuit of FIG. 6 may at first appear redundant, the implementation of the AND function via a series combination of CRP 604 and AraC 606 and via the AND DNA operon 608 serves an important biological function. The redundancy serves to restrict arabinose metabolism to situations where glucose is absent for extended periods of time by requiring that sufficient levels of both active CRP and AraC be present simultaneously in order to simulate AraBAD production and enable arabinose metabolism. Because AraC production is relatively slow, the simultaneous presence of critical levels of active CRP and AraC does not occur when glucose is absent for only a short period of time. Hence the FFL circuit of FIG. 6 ensures that the relatively expensive production of the proteins necessary to process arabinose, a sugar with a higher cost/benefit ratio than glucose, is only initiated if glucose is absent for a sufficiently long time.

As discussed above, factors such as stochastics and time-dependent effects play a significant role in biochemical reaction dynamics. Accordingly, the present invention not only provides electronic models of core biochemical processes, such as induction, activation, transcription, and translation, but also allows additional factors, such as logic-like operators, time delays, and stochastics, to be incorporated into the electronic model in a controlled manner. These electronic analogs of biochemical reaction networks are outlined below.

Figure 7:
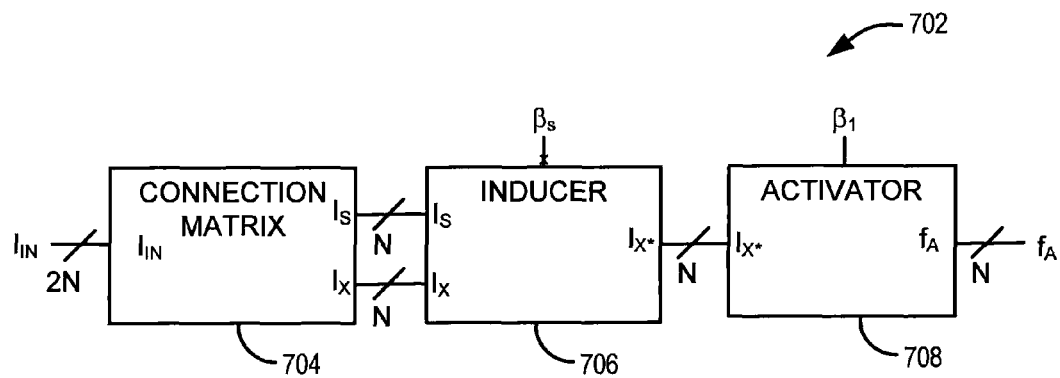
FIG. 7 is a high-level block diagram of a circuit for simulating the induction and binding of transcription activators and deactivators to DNA in accordance with the present invention.

Referring to FIG. 7, a high-level block diagram of a circuit for simulating the induction and binding of transcriptional activators and deactivators to DNA is shown generally at 702. This circuit includes a connection matrix 704 connected to an inducer simulation circuit 706, which is connected to an activator simulation circuit. In this case, each gene can be activated or repressed by N active transcription factors X*, thereby leading to an N-dimensional input function. Active transcription factors can be induced from their inactive forms X by inducer molecules S and each transcription factor may have its own inducer. This results in a total of 2N inputs for the gene, that is, N inducer input signals $I_S$ and N transcription factor input signals $I_X$. The connection matrix 704 allows the concentration of each of these signals to be set equal to any of the 2N external inputs $I_N$. The concentration of any active transcription factor can therefore be modeled using the following equation:

$$I_{X^*} = \frac{I_S I_X}{\beta_{SX} I_0}; \qquad \text{Eqn. 28}$$

where $\beta_{SX}$ is a programmable, dimensionless number that can, for example, be programmed over a 10-bit range between $2^6$ and $\frac{1}{2}^4$ and $\beta_{SX} I_0$ is an electronic analog of the dissociation constant $K_{SX}$. This may be related to a reference chemical concentration $X_0$ as follows:

$$\beta_{SX} I_0 = K_{SX}\left(\frac{I_0}{X_0}\right) \Rightarrow \beta_{SX} = \frac{K_{SX}}{X_0}. \qquad \text{Eqn. 29}$$

Figure 8:
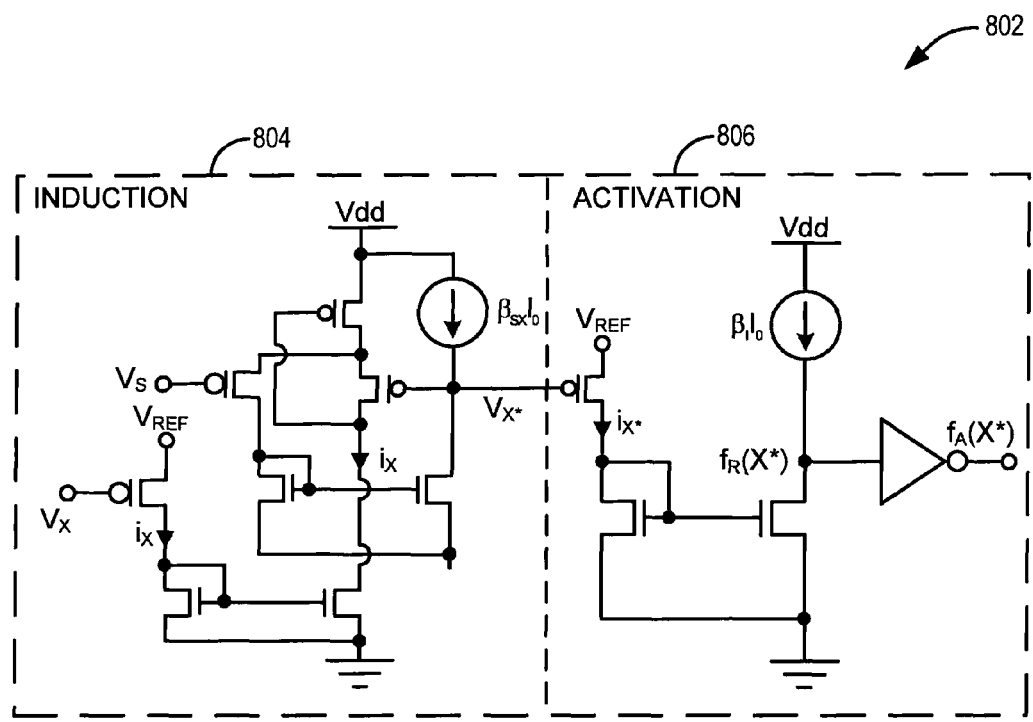
FIG. 8 is a schematic of a circuit that generates an input function of a single transcription factor X, which may be either activating or repressing, in accordance with the present invention.

Referring to FIG. 8, a circuit for implementing Eqn. 28 to model a single inducer-transcription factor pair is shown generally at 802. The circuit includes an induction circuit 804 connected to an activation circuit 806. A given gene can be modeled using N of these circuits 802, which each include a translinear loop to provide the constraint $I_{X^*}(\beta_{SX} I_0) = I_S I_X$. This circuit compares the active transcription factor concentration $X^*$ to the threshold concentration $K_1$ to generate the "logic" activation function $f_A$ and its inverted version $f_R$. In the electronic analog this is performed using the following relationship:

$$f_A(I_{X^*}) = \theta(I_{X^*} > \beta_I I_0);$$

$$f_R(I_{X^*}) = \theta(I_{X^*} < \beta_I I_0) \qquad \text{Eqn. 30};$$

where $\beta_I$ is a dimensionless number whose value can, for example, be programmed over the 10-bit range between $2^6$ and $\frac{1}{2}^4$, and $\theta(x)$ is the threshold function, which is equal to 0 if its argument $x<0$, and equal to 1 otherwise. The value of $\beta_I$ may be set such that the threshold of the electronic analog matches that of the original biological system, that is:

$$\beta_I I_0 = K_I\left(\frac{I_0}{X_0}\right) \Rightarrow \beta_I = \frac{K_I}{X_0}. \qquad \text{Eqn. 31}$$

Eqn. 30 can be implemented using a current comparator circuit requiring only two transistors, such as that included in the circuit 402 of FIG. 4. This acts as an inverter with a current-load source and therefore produces the repression function $f_R$, which may be converted into the activation function $f_A$ using another inverter. The N single-variable activation functions, as modeled by the circuit 802 of FIG. 8, may be combined to model the activation function of an entire gene in accordance with the following equation:

$$I_{ACTV} = I_0 \sum_{i=1}^{s} \beta_i \left[\prod_{j=1}^{n_i} \{f_A(X_K^*), f_R(X_k^*)\}_j\right]; \qquad \text{Eqn. 32}$$

where s is the number of product terms, $I_{ACTV}$ is the activation strength, $k \in \{1, 2, \ldots N\}$, $\beta_i$ are dimensionless numbers, $I_0$ is a reference current, and the Boolean variable ACTV is defined as the logical OR of the same product terms by:

$$ACTV = \qquad \text{Eqn. 33}$$

$$OR\left[\prod_{j=1}^{n_i} \{f_A(X_K^*), f_R(X_k^*)\}, \ldots, \prod_{j=1}^{n_s} \{f_A(X_K^*), f_R(X_k^*)\}_j\right].$$

These equations provide that a gene is being actively transcribed when ACTV=1 with a non-zero activation strength $I_{ACTV}$. The gene is inactive when ACTV=0, which implies that $I_{ACTV}=0$. It is easier to implement these equations if the number of terms in the products and summations, $n_i$ and s, respectively, are fixed. By allowing the terms to be selected from the enlarged set $\{fA, fR, 0, 1\}$, $n_i$ and s can be constant without causing a loss of generality. In this case, all products can have N terms because ignorable inputs for a given product are assigned the value 1. Similarly, S products can be summed to form the output, because unwanted products can be removed by assigning 0 to one or more of the terms within them. For example, it is possible to set N=S=8 for a given chip. In general, however, equations 32 and 32 can be rewritten as:

$$I_{ACTV} = I_0 \sum_{i=1}^{S} \beta_i \left[\prod_{j=1}^{N} \{f_A(X_K^*), f_R(X_k^*), 0, 1\}_j\right] \qquad \text{Eqn. 34}$$

$$ACTV = OR\left[\prod_{j=1}^{N} \{f_A(X_j^*), f_R(X_j^*), 0, 1\}\right];$$

where it is understood that the OR operation has S inputs.

Figure 9:
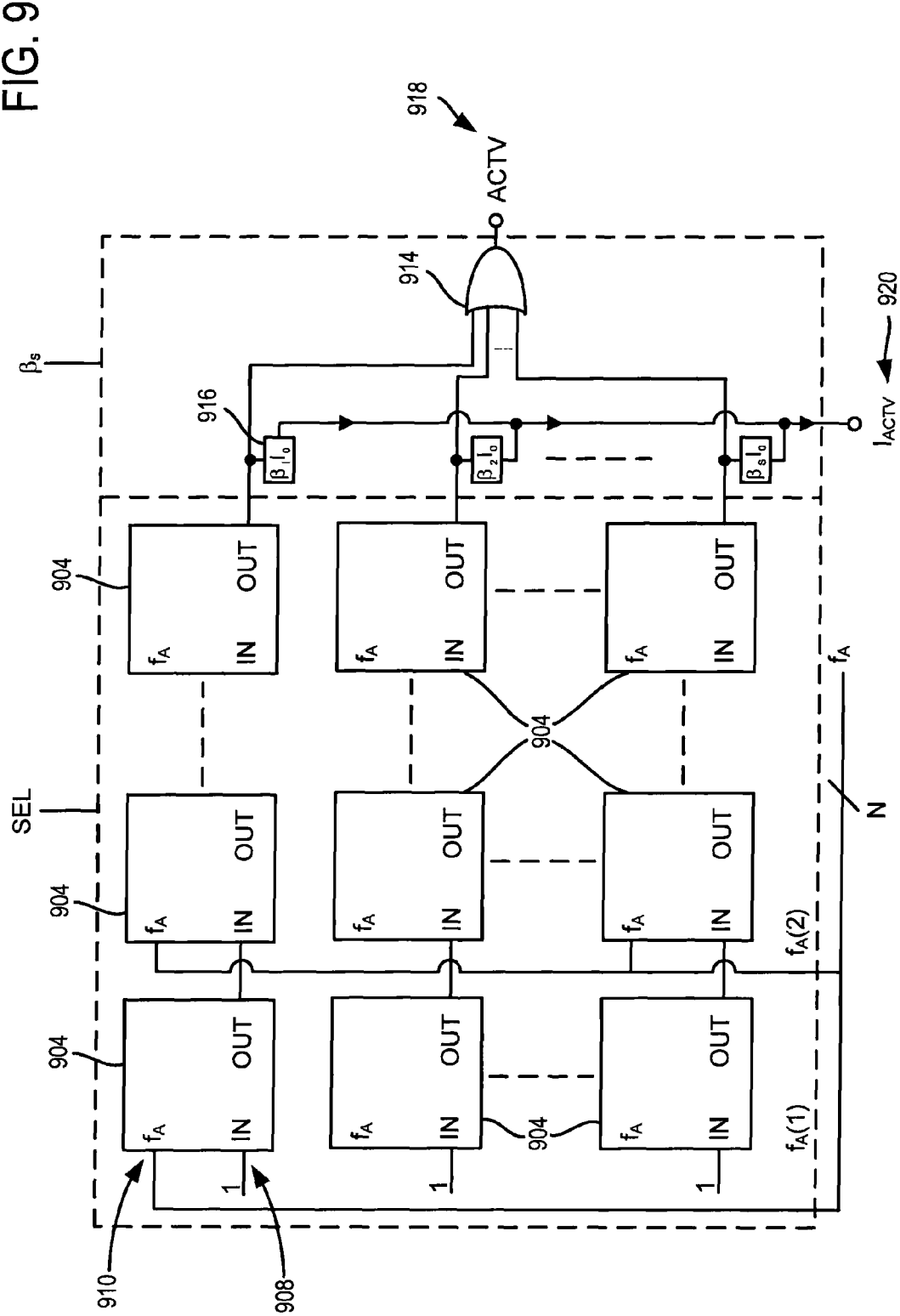
FIG. 9 is a block-diagram of a generalized programmable logic array circuit in accordance with the present invention that simulates the activation of a single gene by combining the effects of a plurality of transcription factors.

Referring to FIG. 9, the above equation may be implemented using a generalization of the programmable logic array (PLA) 902 for synthesizing arbitrary Boolean functions. The exemplary PLA 902 is designed to simulate the activation of a single gene by combining the effects of several transcription factors.

In general, PLAs include an AND-plane and an OR-plane, wherein the AND-plane includes an array of AND gates that compute the minterms of a function, while the OR-plane uses OR gates to combine them into an output. In the present invention, the AND gates may be replaced with more complex combinational logic blocks 904 that each accept the output of a previous block and "AND" it with a member of the set $\{f_A, f_R, 0, 1\}$ to build up a product term. Two control bits SEL(0) and SEL(1) may be fed into each block 904 through a SEL input 906 to determine which member of the set is selected for product formation. Also, two inputs, IN 908 and $f_A$ 910, are the inputs for each gate 904 and OUT 912 is that gate's 904 output. The truth table for each block is shown in Table 1. It should be noted that in the generalized PLA 902, the thick lines denote multi-wire buses. For example, the $f_A$ bus may be N bits wide. In addition, because $f_A$ and $f_R$ are binary-valued functions, $f_R$ equals $\bar{f}_A$, which is the logical negation of $f_A$.

TABLE 1

Truth table of selector blocks in a PLA.

| SEL(1) | SEL(0) | OUT(IN, $f_A$) |
|---|---|---|
| 0 | 0 | 0 |
| 0 | 1 | IN · $f_A$ |
| 1 | 0 | IN · $\bar{f}_A$ |
| 1 | 1 | IN |

The product terms, once formed, can be combined using an S-input OR gate 914 to create ACTV, which is provided to a first output 218 of the circuit 902, or added together with weighting factors $\beta_S$ 916 to generate $I_{ACTV}$ that is provided to a second output 920 of the PLA 902. The values of $\beta_S$ 916 can be individually programmed by transistor DACs over a five-bit range, for example, ¼ to 8. As will be described in detail below, the output of the circuit 902 may be used in wider system models.

Figure 10:
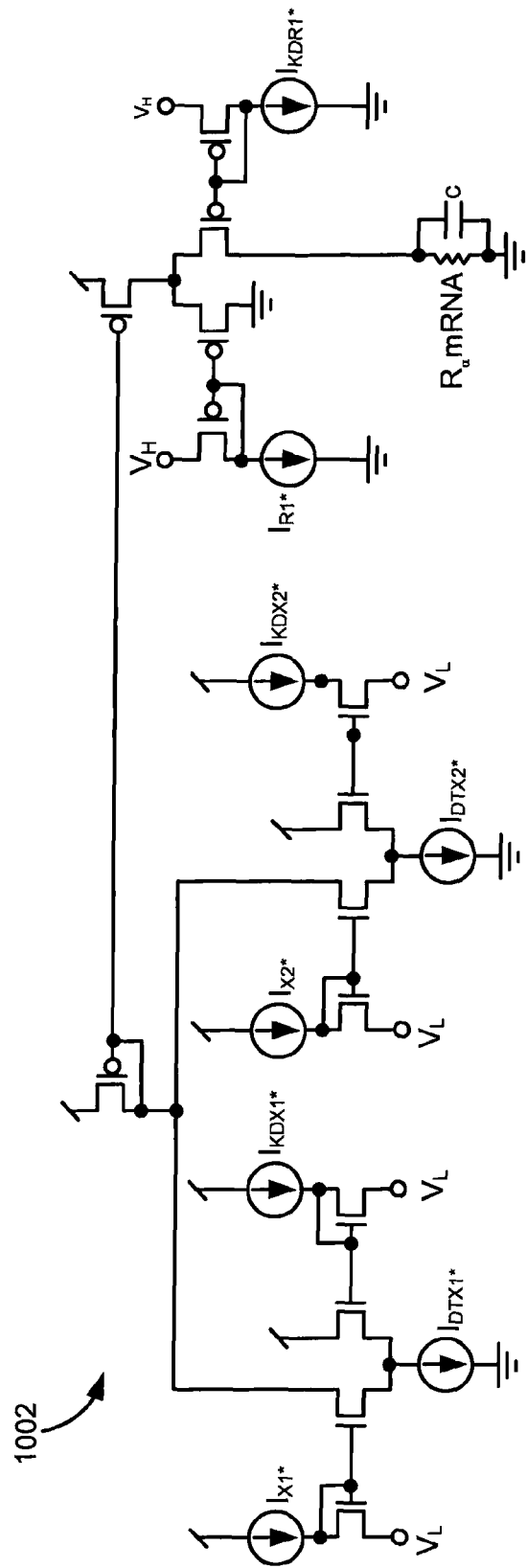
FIG. 10 is a schematic of a DNA analog logic circuit in accordance with the present invention.
Figure 11:
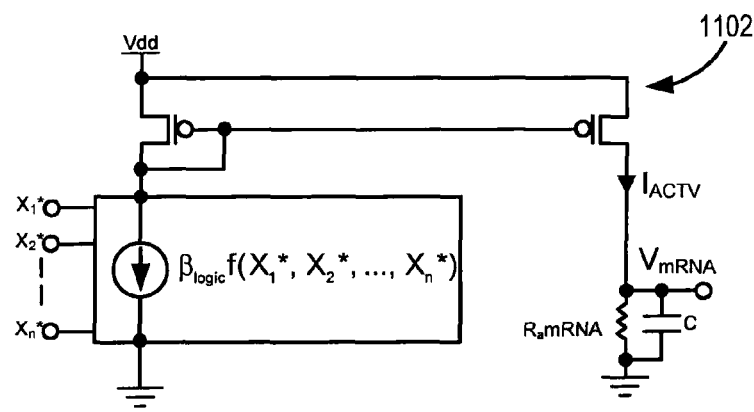
FIG. 11 is a schematic of a hybrid, analog-digital circuit for implementing digital or logic approximations of gene activation functions in accordance with the present invention.

Referring to FIGS. 10 and 11, a DNA 'analog logic' circuit 1002 for simulating logic-like operators is shown. The analog logic circuit 1002 simulates logic-like operators by implementing the following function:

$$I_m = \left[ I_{DTX1*}\left(\frac{\frac{I_{X1*}}{I_{KDX1*}}}{\frac{I_{X1*}}{I_{KDX1*}}+1}\right) + I_{DTX2*}\left(\frac{\frac{I_{X2*}}{I_{KDX2*}}}{\frac{I_{X2*}}{I_{KDX2*}}+1}\right) \right] \left(\frac{1}{1+\frac{I_{R1*}}{I_{KDR1*}}}\right)\left(\frac{R_\alpha^{mRNA}}{1+R_\alpha^{mRNA}Cs}\right); \quad \text{Eqn. 35}$$

which is the analog version of the digital logic function $(X_1^*+X_2^*)\overline{R_1^*}$ and models the effects of two activator transcription factors $X_1^*$ and $X_2^*$ that interact in an OR fashion and share a common resistor $R_1^*$. Further, Eqn. 35 is a consequence of applying subthreshold differential-pair equations to each of the three differential pairs of the analog logic circuit 1002, which model classic monomer Michaelis-Menten binding. Reactions with logic-like operators can also be approximated with digital logic functions using the hybrid analog-digital circuit 1102.

In the hybrid analog-digital circuit 1102, the rate of mRNA production varies with the value of a digital vector input $D_n$ defined by:

$\theta(x)=1$ iff $x>0$ and $0$ otherwise $$D_n = \left(\theta\left(\frac{X_1^*}{K_{DX1*}}-1\right), \theta\left(\frac{X_2^*}{K_{DX2*}}-1\right), \ldots \theta\left(\frac{X_n^*}{K_{DXn*}}-1\right)\right); \quad \text{Eqn. 36}$$

with the rate being a function of $D_n$ given by $$\beta_{mRNA}=\beta_{logic}(D_n) \quad \text{Eqn. 37.}$$

Therefore, for every discrete binary value of $D_n$, for example, "001010", there is a corresponding analog rate of mRNA production, as $\beta_{001010}$ can be listed in a lookup table. In essence, this provides a logic DAC that converts $D_n$ to analog production rates rather than a number-based DAC. It should be noted that the presence of $R_\alpha^{mRNA}$ in the hybrid analog-digital circuit 1102 models mRNA degradation and that translation circuits are represented as in the induction-transcription-translation circuit 1502 of FIG. 15, which will be described in further detail later.

When modeling transcription and translation, it can be assumed that a single mRNA transcript is directly translated into a single protein. While this assumption often leads to an acceptable model of the dynamics of real genes and gene networks, it should be understood that such models are significant simplifications of real cellular processes. For example, prokaryotic genes are often organized into operons that share a common regulatory region and are transcribed into a single "polycistronic" mRNA molecule that encodes for multiple proteins. Conversely, eukaryotic genes are organized into regions that code for proteins known as exons and non-coding regions known as introns. Primary mRNA transcripts contain both exonic and intronic regions that are subsequently removed in a process known as gene splicing to form mature mRNA that can be evenly translated. It should be noted that more complicated models in accordance with the present invention can be developed to include such effects and implement them in hardware.

The present invention models transcription and translation as pseudo-chemical reactions. These processes are not considered "true" chemical reactions because the production of, for example, mRNA from a gene does not result in the gene being consumed. In general, reaction fluxes in such unidirectional systems only change the concentration of products, not reactants. The simplest reasonable model that describes transcription and translation is this way is given by:

$$X \xrightarrow{k} Y \xrightarrow{\gamma} \phi; \quad \text{Eqn. 38}$$

where X and Y are the reactant and product, respectively, of either process and where $\phi$ is a degraded, inactive form of Y. The symbols $k$ and $\gamma$ represent the rates of first-order pseudo-reactions and are respectively known as the synthesis rate and degradation rate of Y. The dynamics of Y can be described by the following equation:

$$\frac{dY}{dt} = kX - \gamma Y. \quad \text{Eqn. 39}$$

The frequency response of this system is that of a first order low-pass filter with the following transfer function:

$$\frac{Y}{X} = \frac{k/\gamma}{1+s/\gamma}. \quad \text{Eqn. 40}$$

The DC gain and time constant of this filter are thus given by $k/\gamma$ and $1/\gamma$, respectively. The time constant $1/\gamma$ may be referred to as the "lifetime" of Y. The dynamics described by the above equations can be exactly represented using a current-mode low-pass filter having dynamics based on the following constraint established by a translinear loop:

$$I_B I_X = (I_A+I_C) I_Y \quad \text{Eqn. 41;}$$

where $I_A$ and $I_B$ are constant currents, $I_C$ is the current flowing through a capacitor C connected to the output of the filter and $I_X$ and $I_Y$ are the concentrations of the input X and output Y, respectively. In transcription, $I_Y$ refers to the concentration of mRNA and $I_X$ equals the activation strength of the gene $I_{ACTV}$. Similarly, for translation, $I_X$ and $I_Y$ refer to the concentration of mRNA and the translated protein, respectively. Thus, the dynamic translinear principle can be used to express:

$$I_C I_Y = \left(\frac{C\phi_T}{k}\right)\frac{dI_Y}{dt}; \quad \text{Eqn. 42}$$

which may be substituted into Eqn. 41 provide:

$$\frac{dI_Y}{dt} = \left(\frac{kI_B}{C\phi_T}\right)I_X - \left(\frac{kI_A}{C\phi_T}\right)I_Y. \qquad \text{Eqn. 43}$$

Eqns. 39 and 43 may then be compared to determine that the systems are dynamically equivalent with a speedup factor of α if:

$$\frac{I_B}{I_0} = \alpha\tau_0 k \qquad \text{Eqn. 44}$$

$$\frac{I_A}{I_0} = \alpha\tau_0 \gamma;$$

where $\tau_0 = C\phi_T/(kI_0)$ and $I_0$ is a binary reference. The currents $I_A$ and $I_B$ are programmable using a binary-weighted DAC such that:

$$\beta_j \equiv \frac{I_j}{I_0} = \beta_{min}(1 + D_j); \qquad \text{Eqn. 45}$$

where jϵA, B and $\beta_{min}$ is the minimum possible value of the dimensionless number $\beta_j$ used to set γ and k. Further, the DAC code $D_j$ is an integer between 0 and ($2^B-1$). For example, an electronic system for modeling transcription and translation may use $\beta_{min}=\frac{1}{4}$ and N=5, thus allowing $\beta_j$ to be varied between ¼ and 8.

Figure 12:
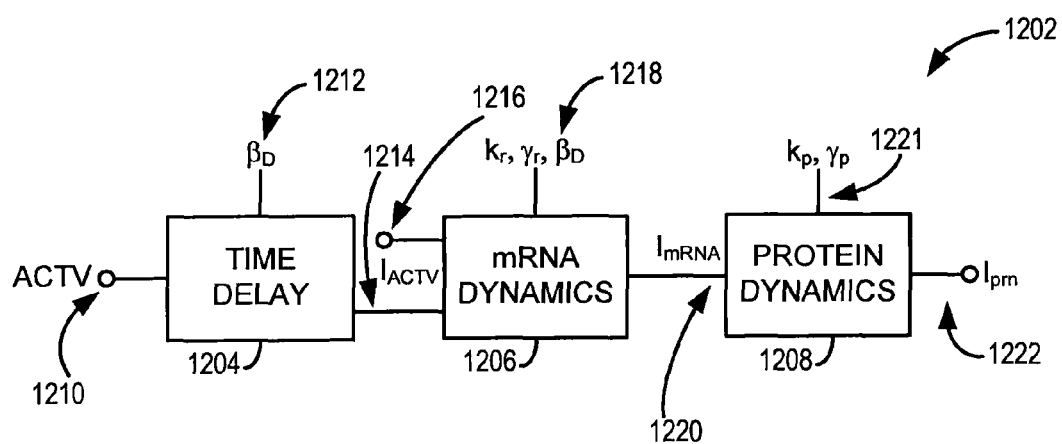
FIG. 12 is a block diagram of circuits that simulates the transcription and translation of a single gene in accordance with the present invention.

Referring now to FIG. 12, a high level block diagram of a circuit for simulating transcription and/or translation is indicated generally at 1202. This circuit includes a first block 1204 that models transcription delay, a second block 1206 that simulates transcription dynamics, and a third block 1208 that simulates the protein dynamics of transcription. The first block 1204 has a first input 1210 that receives, for example, the ACTV signal generated at the first output 918 of the PLA circuit 902 of FIG. 9. The first block 1204 also has a second input 1212 that is configured to delay value $D_{Del}$. The operation of the first block 1204, will be described in further detail below.

Figure 13:
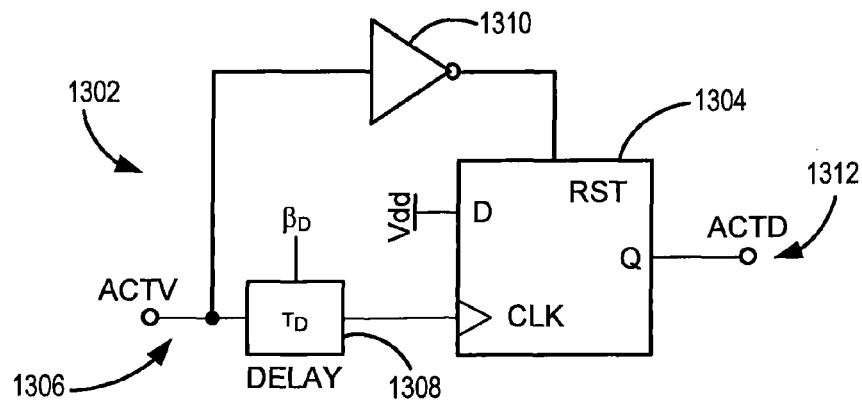
FIG. 13 is a schematic of a circuit for generating sign-sensitive transcription delay in accordance with the present invention.

Referring now to FIG. 13, transcription delays may be modeling using a "delay circuit", as shown generally at 1302. The delay block 1308 within this circuit may be implemented using an M-bit long shift register driven by an on-chip current-controlled ring oscillator running at a frequency $f_{DEL}$ that can be set by a user over, for example, a 10-bit range. The DAC value $D_{Del}$ is linearly proportional to the oscillator frequency, that is, $f_{DEL}=D_{DEL}f_0$, where $f_0$ is constant. The value of $f_0$ is in turn proportional to the global reference current $I_0$ so that $f_0=(I_0/q_{OSC})$, where $q_{OSC}$ depends on the oscillator design and has unit of charge. This provides the following relationship:

$$f_{DEL} = \frac{D_{DEL}I_0}{q_{osc}}. \qquad \text{Eqn. 46}$$

The quantity $q_{OSC}$ can be viewed as the total charge supplied to the capacitors within the oscillator during one oscillation cycle and this charge ultimately comes from the power supply. For ring oscillators, $q_{OSC}$ is approximately equal to $NC_LV_{OSC}$, where N is the number of stages, $C_L$ is the capacitance at each stage, and $V_{OSC}$ is the oscillation amplitude. The activation signal ACTV provided to an input of the circuit 1302 and fed through a delay 1308 to act as the clock input for the flip-flop 1304 and through an inverter 1310 to a reset input of the flip-flop 1304. The activation signal ACTV is not synchronized with respect to the oscillator and, as a result, goes high at a random time within the oscillator cycle, thus providing a delay that includes two parts. The first part includes a time between ACTV going high and the next rising oscillator edge and is a uniformly-distributed random number between 0 and $1/f_{DEL}$. If oscillatory jitter is negligible, then the second part of the delay is fixed and equal to M cycles of the oscillation frequency. Thus, the total delay is given by:

$$T_D = \left(\frac{M+1/2}{f_{DEL}}\right)\left(1 + \frac{\chi}{M+1/2}\right) \qquad \text{Eqn. 47}$$

$$= \frac{q_{osc}}{I_0}\left(\frac{M+1/2}{D_{DEL}}\right)\left(\frac{1+\chi}{M+1/2}\right).$$

where χ is a random variable uniformly distributed between ±½. The mean value and standard deviation of the delay are given by:

$$\overline{T}_D = \frac{q_{osc}}{I_0}\left(\frac{M+1/2}{D_{DEL}}\right) \qquad \text{Eqn. 48}$$

$$\sigma_{TD} = \frac{q_{osc}}{I_0}\left(\frac{1}{\sqrt{12\,D_{DEL}}}\right).$$

From this equation, the SNR of $T_D$ is given by $T_D^2/\sigma_{TD}^2 = 12(M+\frac{1}{2})^2$. Thus, the mean value and SNR of transcription delay can be set using $D_{DEL}$ and M, respectively. For example, a chip having a fixed value M=16 can provide an SNR of 35 dB, $q_{OSC}=1.5\times10^{-12}$, and $C=9.2\times10^6$ q for $V_{OSC}=V_{DD}/2=0.90$ V, where q is the electronic charge. For a typical value of $I_0=10$ nA this chip may provide $f_0=6.8$ kHz, thus allowing $T_D$ to be varied between 38 μs and 39 ms. Thus, a signal, ACTD, provided at an output 1312 of the circuit 1302 that is randomly delayed with respect to the signal ACTV provided at the input 1306. A user may bypass the delay circuit 1302 entirely, however, and set $T_D=0$.

Figure 14:
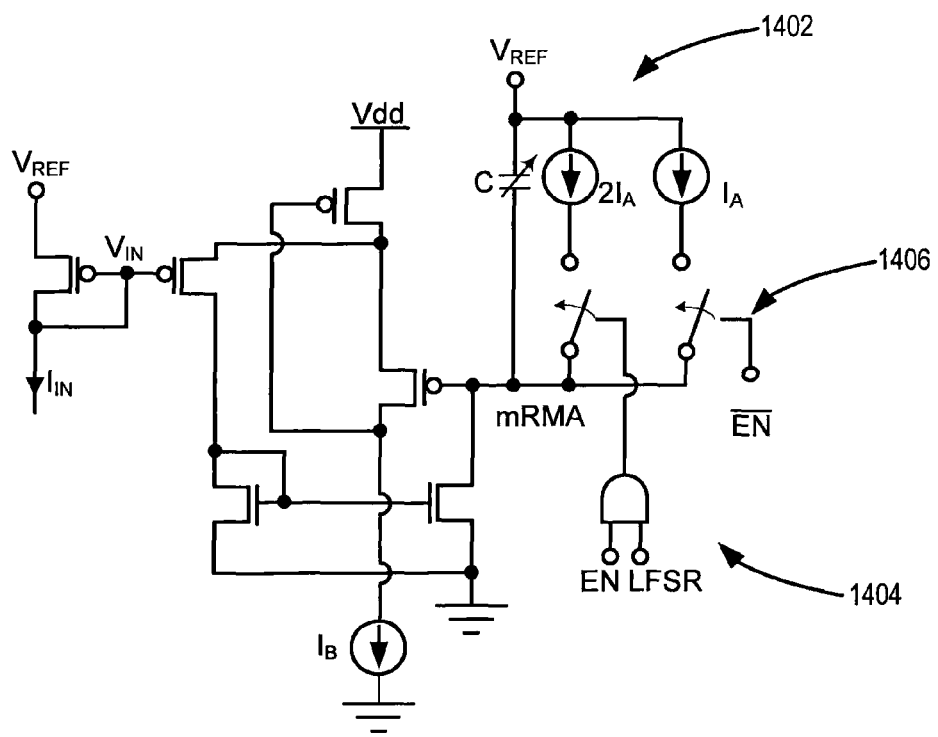
FIGS. 14 and 14a are schematics of simplified circuits that simulate the genetic process of transcription in accordance with the present invention.

Referring to again to FIG. 12, the time delayed output can be fed into the transcription stage 1206 at a first input 1214, the $I_{ACTV}$ signal can be provided to a second input 1216 by, for example, the second output 920 of the PLA circuit 902 of FIG. 9, and the reaction components β, k, and γ (here $β_{snr}$, $k_r$, and $γ_r$) can be provided to a third input 1218 to control the simulated transcription of a DNA sequence into mRNA. Referring to FIG. 14, transcription can be modeled using a translinear, low-pass filter circuit such as that indicated generally at 1402. This circuit is similar to that described above with respect to FIG. 8, but is simplified and includes a noise-generation sub-circuit 1404 for adjusting the SNR of the simulation.

The noise generation sub-circuit 1404, which will be discussed later in further detail, can be enabled or disabled by setting a control bit EN to 1 or 0, respectively, to close or open a plurality of switches 1406. While the current discharging in the output capacitor C has an average value of $I_A$ in both cases and results in similar average waveforms, this average is produced by a constant current of value $I_A$ when EN=0, and a current that switches between $2I_A$ and 0 with a 50% duty cycle when EN=1. In the latter case, the switching waveform is set by a random or pseudo-random pulse generator. The pulses produced by this generator generally obey Poisson statistics, that is, the number of pulses that occur in a fixed time interval should follow the Poisson distribution. In the particular embodiment shown in FIG. 14 the pulse generator has been implemented using a linear feedback shift register. Switches in the circuit 1402 may be implemented as differential, or current steering, structures that significantly reduce "switching glitches" that result from charge injected into nearby nodes via capacitive coupling.

The log-compressed version of the input current $I_{IN}$ is denoted by $V_{IN}$ and it may be shown that the transfer function of this filter in the noiseless case when EN=0 is given by:

$$\frac{I_{mRNA}}{I_{IN}} = \frac{I_B/I_A}{1+s(\tau_0 I_0/I_A)}; \quad \text{Eqn. 49}$$

where $\tau_0 = C\phi_T/(kI_0)$ and it is contemplated that the values of $I_A$, $I_B$, and C can be varied over a 5-bit range. To model mRNA dynamics, the selection $I_A$ and $I_B$ may be based upon mRNA synthesis and degradation rates, k and $\gamma$, respectively. Once $I_A$ and $I_B$ are set, the transfer function of Eqn. 49 is dynamically equivalent to the chemical transfer function of Eqn 40. When ACTV=0, which implies the gene is "off", $I_{IN}=I_{OFF}$, where $I_{OFF}$ is a global constant that may be user-controlled. Alternately, when ACTV=1, the gene is "on" and $I_{IN}=I_{ACTV}$, though the input to the translinear low-pass filter circuit 1402 as a function of the activation signal ACTV can be further changed using a network of switches. The steady-state mRNA concentrations as predicted by Eqn. 49 are then given by:

$$I_{mRNA,ON} = \frac{I_{ACTV} I_B}{I_A} \quad \text{Eqn. 50}$$

$$I_{mRNA,OFF} = \frac{I_{OFF} I_B}{I_A}.$$

The on/off ratio, which may have biological significance, can then be defined as the ratio steady-state mRNA concentration in the two cases and is given by:

$$R_{mRNA} = \frac{I_{mRNA,ON}}{I_{mRNA,OFF}} = \frac{I_{ACTV}}{I_{OFF}}. \quad \text{Eqn. 51}$$

This scheme provides two advantages. First, it provides independent control of $I_{mRNA, ON}$ and $R_{mRNA}$, which, for example, may be changed by varying $I_A$ and $I_{ACTV}$, respectively. Second, by making $I_{OFF}>0$, it can be ensured that the transistors within the translinear low pass filter 1402 are saturated and, concordantly, that the transfer function of Eqn. 49 is valid.

Referring again to FIG. 12, thus, as described above with respect to FIG. 14, the transcription stage 1206 generates $I_{mRNA}$, which is provided to a first input 1220 of the third block 1208 along with the reaction components k and $\gamma$ (here $k_p$ and $\gamma_p$), which are provided on a second input 1221.

Referring to FIGS. 12 and 14, a circuit that models translation is generally similar to the translinear low-pass filter circuit 1402 modeling transcription. However, the translation circuit does not include the switches 1406 and $I_A$ is generally a constant current source. Accordingly, this circuit takes as an input $I_{IN}=I_{mRNA}$ and generates a current $I_{prn}$ at an output of the simulating circuit 1202, which is the electronic analog of protein concentration. It can be shown that $I_{mRNA}>0$ in both active and inactive states and, as a result, transistors within the translation filter are generally saturated in both these states. In addition, the parameters of this filter, such as $I_B$, $I_A$, and C can be set by a user, for example, using 5-bit DACs.

Figure 14A:
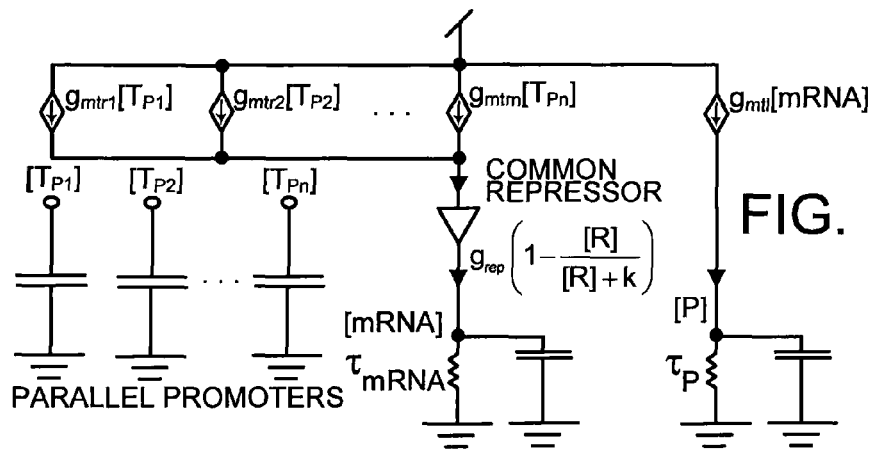

It should be noted that other circuits in accordance with the present invention can be used to model genetic processes. For example, an additional electronic circuit for simulating the processes of transcription and translation for a single gene is provided in FIG. 14a.

Figure 15:
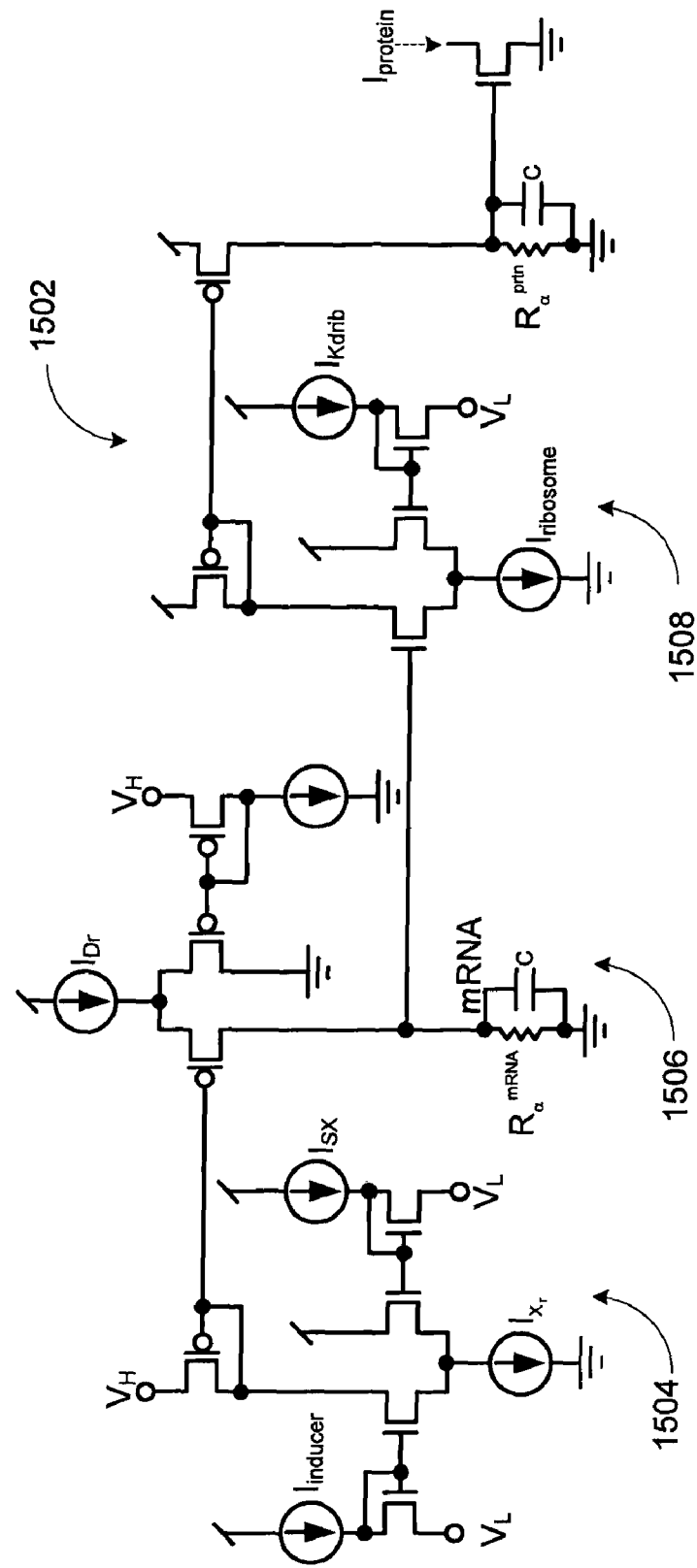
FIG. 15 is a schematic of a circuit for simulating the genetic processes of activation, transcription and translation.

As a further example, referring now to FIG. 15, an induction-transcription-translation circuit 1502 is shown. The circuit includes an induction module 1504, a transcription module 1506, and a translation module 1508. If the inducer concentration $I_{inducer}$ is significantly greater than $I_{SX}$, which is the $K_d$ for inducer-transcription-factor binding, then most of the transcription-factor molecules X will be transformed into an active state X*. The current output of the subthreshold pair the represents induction quantitatively models this process by:

$$I_{X^*} = I_{XT}\left(\frac{\frac{I_{inducer}}{I_{SX}}}{\frac{I_{inducer}}{I_{SX}}+1}\right). \quad \text{Eqn. 53}$$

This provides an exact model of Michaelis-Menten binding, as per Eqn. 53, where $I_{XT}$ represents the total concentration of transcription-factor, $X_T$, whether activated or not. Similarly, if the activated transcription-factor concentration $I_{X^*}$ is significantly greater than $K_d$, then the rate of production of mRNA transcripts by the enzyme RNA polymerase will be near its maximal value. This assumes, without loss of generality, that the transcription factor in question is an activator. The current model, $I_m$ of the subthreshold differential pair that represents transcription quantitatively models this process by:

$$I_m = I_{DT}\left(\frac{\frac{I_{X^*}}{I_{Kd}}}{\frac{I_{X^*}}{I_{Kd}}+1}\right). \quad \text{Eqn. 54}$$

In this equation, $I_m$ represents the rate of mRNA production, while $I_{DT}$ denotes the maximal rate of mRNA production. The equation also suggests that the absence of the activator reduces mRNA production to zero, though a constant-current term may also be added to model a basal mRNA production rate that occurs when there is no activator present. Eqn. 54 can be converted into a repressor equation by using current from the other arm of the transcription differential-pair in the induction-transcription-translation circuit 1502. The current $I_m$ leads to a final mRNA concentration that is described by a Laplace-transform low-pass filter (LPF) equation as follows:

$$I_{mRNA}(s) = I_m(s)\frac{R_\alpha^{mRNA}}{1+R_\alpha^{mRNA}Cs}. \quad \text{Eqn. 55}$$

In Eqn. 55 and the circuit 1502, $I_{mRNA}/R_\alpha^{mRNA}$ is the rate of degradation of mRNA due to enzymes that actively degrade mRNA in a linear fashion and C is the volume of the reaction compartment of the cell. The time course of transcription is typically determined by the $R_\alpha^{mRNA}C$ time constant since inducer binding is relatively fast. While the induction-transcription-translation circuit 1502 represents mRNA as a voltage variable for simplicity, the $R_\alpha^{mRNA}C$ circuit can be replaced by a current-input, current-output LPF that outputs an $I_{mRNA}$ current instead of an mRNA output voltage. If $I_{mRNA}$ represents the mRNA concentration, the process of translation may be represented using the overall equation:

$$I_{protein}(s) = I_{ribosome} \left( \frac{\frac{I_{mRNA}}{I_{Kdrib}}}{\frac{I_{mRNA}}{I_{kdrib}} + 1} \right) \left( \frac{R_\alpha^{prtn}}{1 + R_\alpha^{prtn}Cs} \right); \quad \text{Eqn. 56}$$

with the parameters show in the circuit 1502. Typically the protein degradation time constant $R_\alpha^{prtn}C$ is the largest time constant in the overall process, which can range from 30 minutes in bacteria in high-growth medium to over 20 hours in human cells. In fact, some proteins may not be degraded at all. Eqns. 53 to 56 represent the core of gene-protein dynamics when chemical binding occurs between two monomers. However, a transcription-factor frequently has maximal binding efficacy to DNA when it is a dimer, which has two identical molecules bound to each other, or a quadrimer, which has four identical molecules bound to each other. In such situations Eqn. 54 can be well approximated by an equation of the form:

$$I_m = I_{DT} \frac{\left(\frac{I_{X^*}}{I_{Kd}}\right)^n}{\left(\frac{I_{X^*}}{I_{Kd}}\right)^n + 1}; \quad \text{Eqn. 57}$$

where n=2 in the case of dimer binding and n=4 in the case of quadrimer binding. The parameter n, which may be referred to as the "Hill coefficient", is implicitly 1 in Eqns. 53 to 56. At large Hill coefficients, Eqn. 57 can be described using a digital approximation. For example, the hybrid analog-digital circuit 1102 provides an approximate representation of DNA-protein interactions that performs best at high Hill coefficients. If the transcription factor is an activator, it may be assumed that mRNA transcript production is at its maximal rate $I_{DT}$ when $I_{X^*} > K_d$ and 0 otherwise. If the transcription factor is a repressor, it may be assumed that mRNA transcript production is at 0 when $I_{X^*} > K_d$ and $I_{DT}$ otherwise. Circuits to create Hill coefficients with any analog value, for example, from 1 to 4, can be designed by exploiting a strategy similar to the creation of power-law coefficients in automatic gain control (AGC) circuits, in which the input diode-connected transistors in the induction-transcription-translation circuit 1502 are replaced by a transistor with a buffered wide-linear-range transconductor (WLR) of transconductance $G_1$ from its drain to gate and a buffered WLR of transconductance $G_2$ from its gate to a reference so that programming of $G_1$ and $G_2$ with DAC currents ensures that a power-law of approximately $(G_1+G_2)/G_1$ is obtained.

Figure 16A:
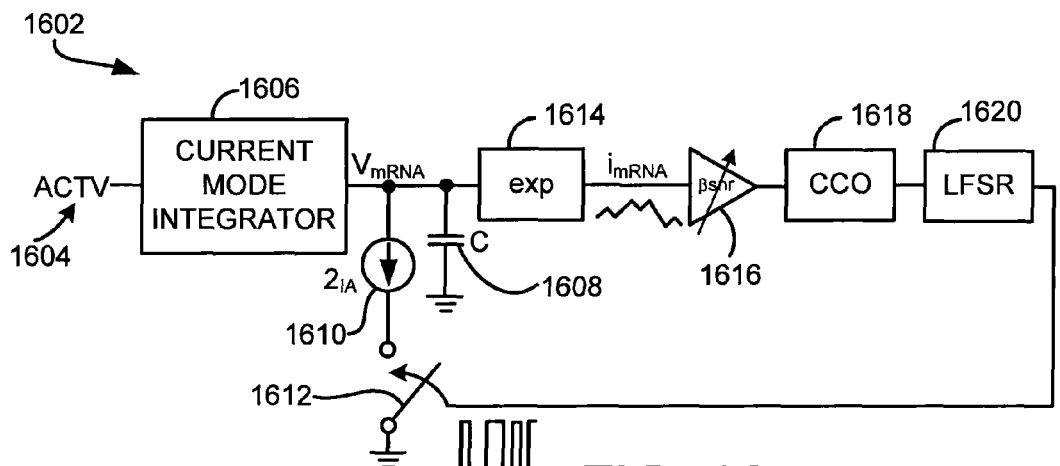
FIGS. 16a and 16b are schematics of circuits for adjusting the signal-to-noise ratio of simulated chemical species in accordance with the present invention.

Referring to FIG. 16a, Poisson noise in mRNA-production flux can be mimicked by Poisson current noise in a manner similar to that discussed previously for protein-production flux. However, noise levels in mRNA production for some genes are so high that extremely low currents and small capacitances become necessary to mimic the low SNR in biology using electronics. This can result in electronic noise that is difficult to control and predict. Therefore, it can be advantageous to artificially introduce a controlled amount of noise into a relatively quite electronic circuit to artificially mimic high-noise signals in biology.

This can be achieved using the noise-generation circuit 1602, which receives the ACTV signal at an input 1604 and feeds it through a current mode integrator 1606. The current mode integrator 1606 is coupled to an output capacitor 1608 and current leak, $2I_A$, 1610 that implement a current-mode version of the $R_\alpha^{prtn}C$ low-pass filter of the hybrid-analogue digital circuit 1102. In contrast to the constant $2I_A$ of traditional current-mode integrators, the $2I_A$ in the noise-generation circuit 1602 is coupled to a switch 1612 that can be randomly switched on and off with a duty cycle of, for example, 0.50. Thus, the leak current 1610 has an average value of $I_A$, but includes a stochasticity due to the random switching. The log voltage on the current-mode capacitor 1608 is exponentiated 1614 and converted to a current $I_{mRNA}$ that encodes the level of mRNA as in any given current-mode circuit. The current $I_{mRNA}$ is passed through an amplifier 1616 having a gain of $\beta_{snr}$ and employed to control the frequency, $f_{CCO}$, of a current-controlled oscillator (CCO) 1618. The output switching frequency of the CCO 1618 is proportional to $I_{mRNA}$ according to $f_{CCO}=(I_{mRNA}/q_{CCO})$, where $q_{CCO}$ depends on $\beta_{snr}$ and COO 1618 design parameters. Therefore, as mRNA levels rise, the control current rises proportionally and the switching frequency increases. A random or pseudo-random pulse generator, represented in this particular embodiment by a linear feedback shift register (LFSR) 1620 converts the digital output of the CCO 1618 to a randomly switching signal via a pseudo-random-number generation technique. Thus, the output of the LFSR 1620 randomly switches the switch 1612 and, thus, the $2I_A$ current 1610 on and off with a switching frequency $f_{CCO}$ proportional to the mRNA level encoded by $I_{mRNA}$. Consequently, as mRNA levels rise due to a higher mRNA production rate, the arrival rate $f_{CCO}$ of charge packets with a value $I_A/f_{CCO}$ increases, even though the mean value of current stays at $f_{CCO}(I_A/f_{CCO})$ $=I_A$. The noise PSD of the switching current at the log-voltage node with $q=I_A/f_{CCO}$ and a mean current of $I_A$ is given by the following shot-noise formula:

$$\Delta I_{psdout}^2 = 2\left(\frac{I_A}{f_{CCO}}\right) I_A. \quad \text{Eqn. 58}$$

If the conductance at this node is G(f), then the noise PSD is given by:

$$\Delta I_{psdout}^2(f) = 2\left(\frac{I_A}{f_{CCO}}\right) I_A \frac{g_m^2}{G(f)^2} \quad \text{Eqn. 59}$$

$$= 2\left(\frac{I_A}{(I_{mRNA}/q_{CCO})}\right) I_A \frac{I_{mRNA}^2/(\phi_t/\kappa)^2}{G(f)^2}$$

$$= 2q_{CCO} \frac{I_A^2}{G(f)^2(\phi_t/\kappa)^2} I_{mRNA};$$

while the output signal power is given by:

$$I_{out}^2 = \frac{I_A^2 I_{mRNA}^2}{G(f)^2(\phi_t/\kappa)^2}; \quad \text{Eqn. 60}$$

since the DC input from the current mode integrator must be $I_A$ as well. By comparing Eqns. 59 and 60, it can be noted that the ratio of the output signal power and output noise PSD behave exactly as expected for a classic Poisson shot-noise current source, except that the charge on the electron has been replaced by $q_{CCO}$. Thus, the value of $q_{CCO}$ serves effectively like the electron charge, it can be increased to produce more noise (by decreasing $\beta_{snr}$ to reduce $f_{CCO}$) or decreased to produce noise (by increasing $\beta_{snr}$ to increase $f_{CCO}$).

Figure 16B:
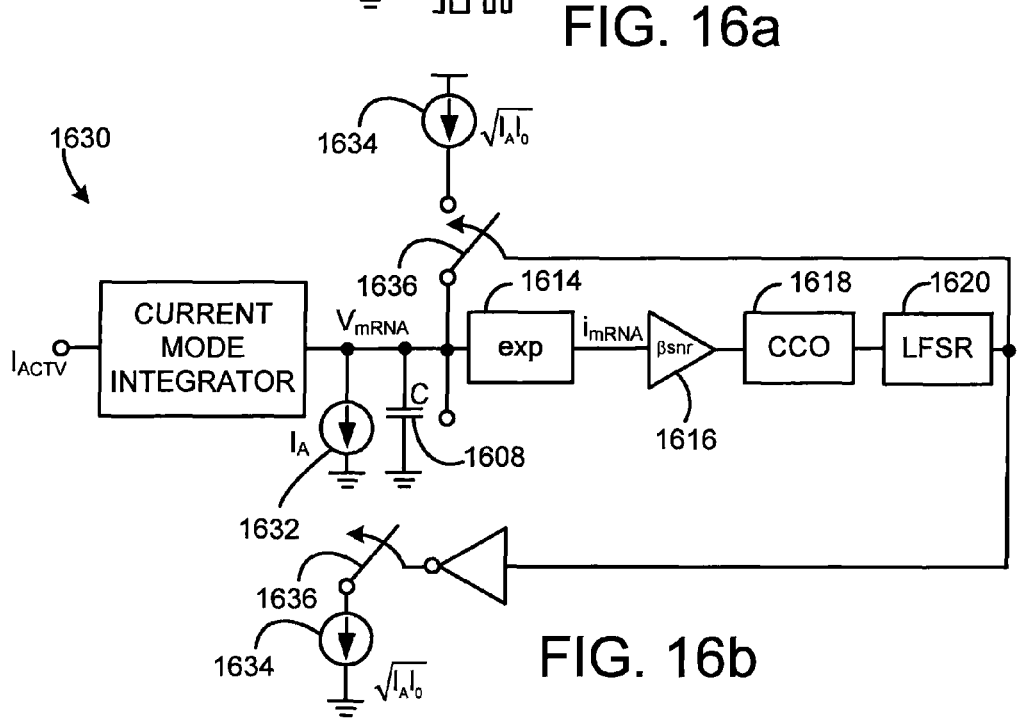

The input 1604 in the noise generation circuit 1602 is a logical signal that is activated when a switching transition in $D_n$ leads to mRNA production. Transients in ACTV will lead to $R_\alpha^{prtm}C$-like dynamics in mRNA level and, as mRNA levels change, the output noise of the noise generation circuit 1602 will change accordingly, thereby ensuring that noise dynamics and signal dynamics are correlated as in any real biological or artificial system. It should be noted that, in addition to controlling the SNR of mRNA concentrations, noise generation circuits similar to the circuit 1602 may be employed in accordance with the present invention to control the stochastic properties of any chemical species being simulated. For example, FIG. 16*b* shows a similar noise generation circuit having a current source 1632 producing a continuous current $I_A$ and two current sources 1634 connected to switches 1636 that together inject into the circuit two pseudo-random switched currents of value $\sqrt{I_0 I_A}$ with opposite polarities at $v_{mRNA}$.

Figure 17A:
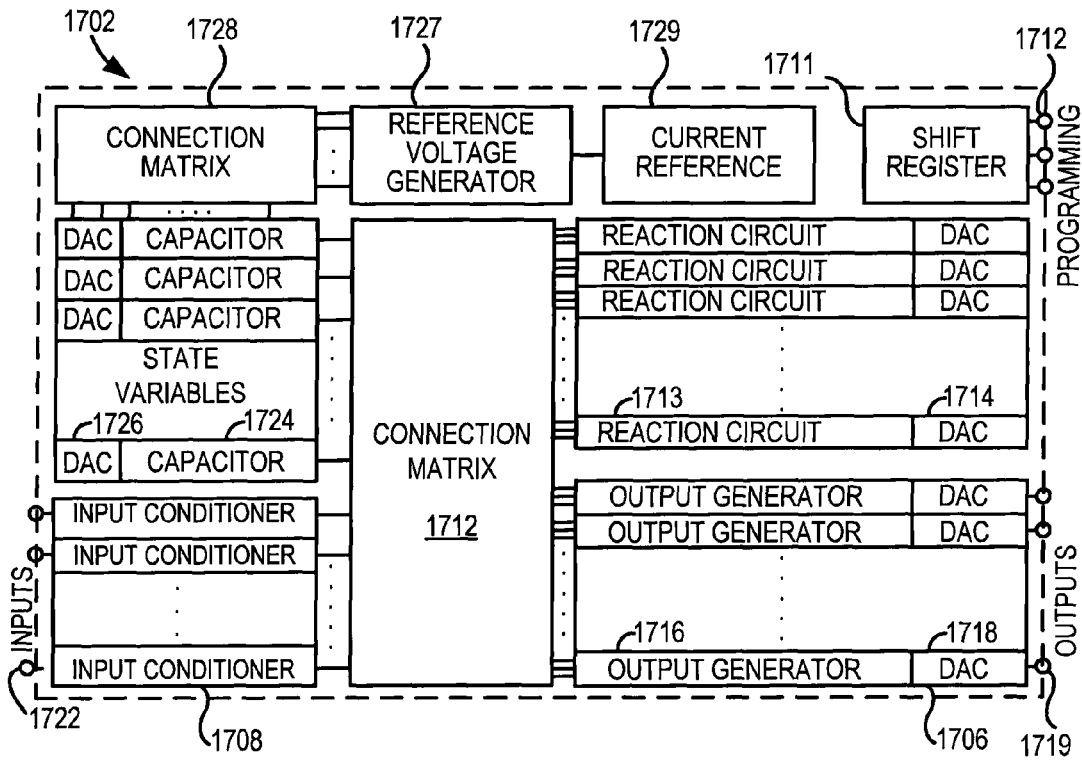
FIGS. 17a to 17c show block diagrams for electronic chips that simulate chemical and biochemical reaction networks and their interactions in accordance with the present invention.

Referring to FIG. 17, analog and hybrid-analog digital electronic circuits, such as those described above, may be incorporated onto electronic chips so that large-scale chemical and biochemical networks may be simulated efficiently. For example, a 1.5 mm×1.5 mm chip fabricated using a 0.18 µm CMOS process and having 81 second-order reaction blocks, 40 first order blocks, 40 zeroth order reaction blocks, 32 state variables, 16 inputs, and 8 outputs may be employed to model chemical reaction networks. A high level block diagram of this chip 1702 is depicted in FIG. 17*a*. The chemical reaction simulation chip 1702 includes a reaction simulation module 1704, output module 1706 input conditioning module 1708 and state variable storage module 1710 that are all connected to a primary connection matrix 1712. The chip 1702 also includes a shift register 1711 that can be programmed via inputs 1712. The reaction simulation module 1704 includes a set reaction circuits 1713, such as those discussed above, each connected to a set of DACs 1714. The output generating module includes a set of output generator circuits 1716, which will be discussed in further detail below, each connected to a DAC 1718 having an output 1719. The input conditioning module includes a plurality of input conditioner circuits 1720 connected to inputs 1722. The state variable storage module 1710 includes a set of capacitors 1724 configured to store state variables that are each connected to capacitor DACs 1726. The state variable storage module 1710 is also connected a reference voltage generator 1727 via a secondary connection matrix 1728. The reference voltage generator 1727 is also connected to a current reference module 1729, from which it receives reference currents.

The main connection matrix 1712 represents an array of programmable switches that makes the topology of the network completely arbitrary and the parameters of the network topology, such as reaction rates, initial conditions, volume compartments of reactions, and the identity of molecular species, are individually programmable via reprogrammable digital bits. On these chips, state variables may be stored on the capacitors 1724 in log-compressed form, while the value of the capacitors can be set individually by the capacitor DACs 1726, thereby allowing the simulation of systems where reactants and products are present in compartments with different volumes. Likewise, the reference voltage generator 1726 can be used to determine the allowable set of initial conditions that can be set on the capacitors 1726 and a secondary connector matrix 1728 allows a user to select an arbitrary member of the set for each state variable.

Figure 17B:
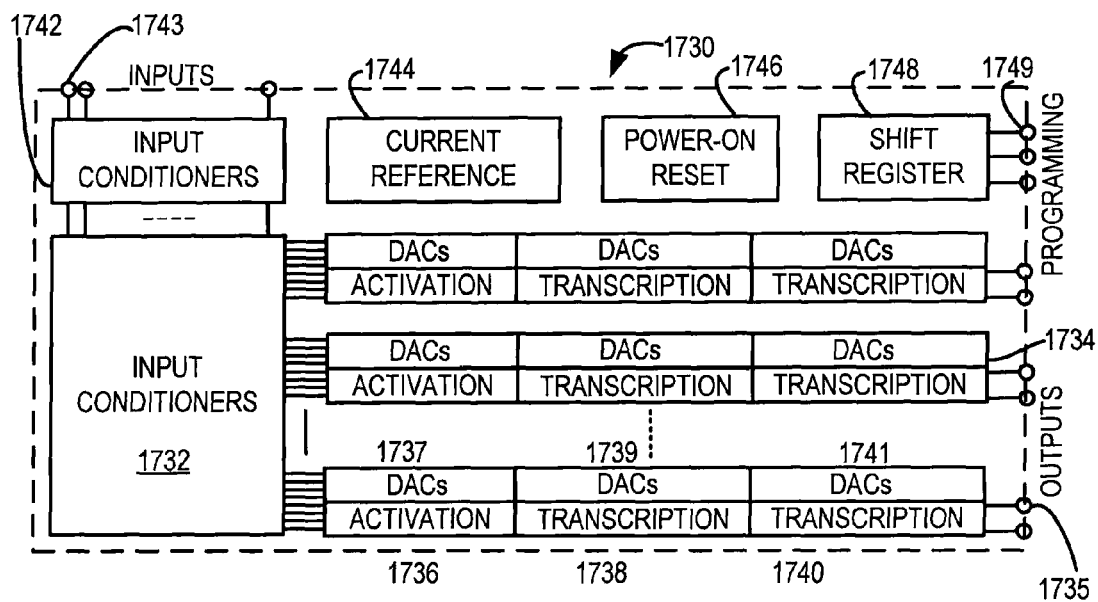

Referring to FIG. 17*b*, an exemplary high level diagram for a genetic network chip 1730 having 6 gene circuits and 16 external, off-chip, inputs fabricated using an 0.18 µm CMOS process is shown. The genetic network chip 1730 includes a connection matrix 1732 connected to a set of genetic simulation modules 1734, each having a outputs 1735. More specifically, the genetic simulation circuits include an activation circuit 1736 connected to a set of activation DACs 1737, a transcription circuit 1738 connected to a set of transcription DACs 1739, and translation circuit 1740 connected to a set of translation DACs 1741. Also connected to the connection matrix 1732 is an input conditioner 1742 having inputs 1743 that will be discussed in further detail later. The genetic network 1730 also includes a current reference module 1744, a power-on reset module 1746, and shift register 1748 that can be programmed via inputs 1749.

The connection matrix 1732, which includes an array of programmable switches, allows any external input to act as an inducer or transcription factor for any gene. Programmable parameter values can be set on chip for individually-addressable transistor or capacitor DACs and both the connection matrix and DACs may be programmed by loading bits into a 30-bit global shift register 1748. The global shift register 1748 can be divided into two sections, a 20-bit data section and 10-bit address section, which may be further split into the 4 most significant digits that are used to locate a gene and the 6 least significant digits that are used to locate sub-circuits within the gene.

Figure 17C:
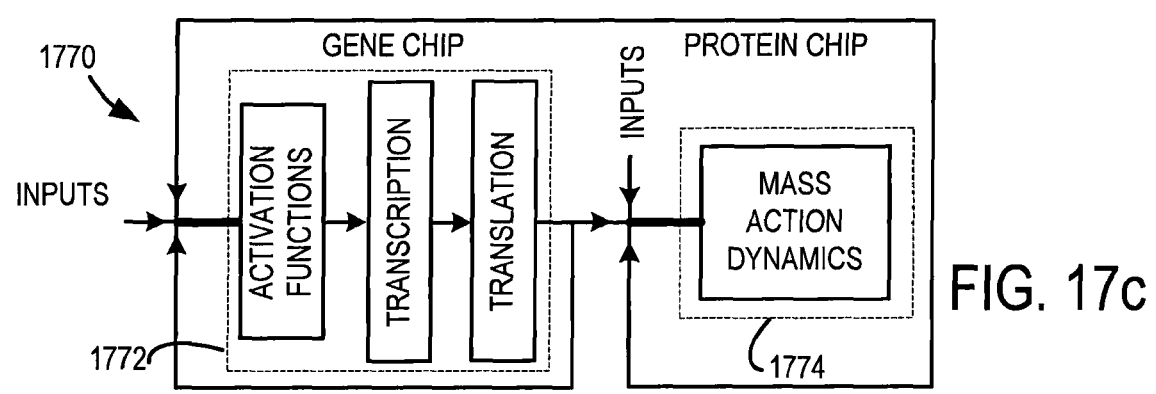

Referring to FIG. 17*c*, a reaction network simulation system 1770 including a "gene chip" 1772 for modeling genetic networks and a "protein chip" 1774 for modeling chemical networks may used to model complicated biochemical pathways involving genes, proteins, and their many interactions. As depicted, the hybrid system allows the gene and protein chips to interact closely with each other. Thus, the chemical simulator will accept translated proteins as inputs, while its outputs can be fed into the genetic simulator where they can act as transcription factors. Such systems can interface with standard desktop computers by implementing a universal serial bus (USB) interface and the system may additionally include analog-to-digital converters, flash memory, and a micro-controller that acts as a interface between the reaction simulation system and the desktop computer. The micro-controller may handle all low-level communications with the chips, including programming and data acquisition, for example, allowing a user to perform multiple simulation runs, store the results in the on-board memory, perform simple analyses, and extract meaningful information, but without transferring large amounts of raw data to the computer, thus alleviating input/output bandwidth bottlenecks that commonly affect high-performance computing.

It is contemplated the these electronic chips and other circuit analogies can be used to describe many other aspects of cellular circuits. For example, the DNA-protein circuit 1202 of FIG. 12 shows that transcription and translation can be viewed as two successive gain stages of amplification, such that input-referred noise in the first gain stage is more important. Robustness, efficiency, analog-digital, and other feedback-circuits-and-systems tradeoffs occur in cells just as in ultra-low-power analog and mixed-signal circuit design. Ultra-low-power analog electronic circuits face very similar tradeoffs to cells, because of their need to operate quickly, accurately, and robustly in spite of mismatched and noisy components and signals due to limited levels of available power and space. It is therefore contemplated that the present invention may be employed to perform circuits-and-feedback analysis of stochastics and system dynamics in cells. For example, small-signal and stochastic analyses may be performed to estimate equilibrium molecular concentrations in a cell. Likewise, large-scale signal analyses may be performed to determine the effect on a chemical reaction system of keeping one molecular concentration constant while varying another. Furthermore techniques for performing noise analysis on circuits may be "ported over" to biological systems to analyze stochastics in cells on a large cell. For example, it would be possible to model the stochastic variation of protein concentrations within cells, which is highly significant for predicting cellular response to environment conditions and drug treatments. Similarly, feedback techniques may be employed to investigate system-and-network dynamics within a cell from the "device dynamics" of its individual protein-protein and DNA-protein constituent biochemical reactions.

In addition to the previously-described chemical reaction circuits, additional circuits may be included in electronic systems for modeling chemical reactions, such as the chips described above. For example, state variables are generally stored on capacitors and distributed to various reaction circuits as log-compressed voltages, rather than currents. Distributing voltages is advantageous, because it allows less long-distance routing and lower noise due to the elimination of one or more current mirrors.

Figure 18:
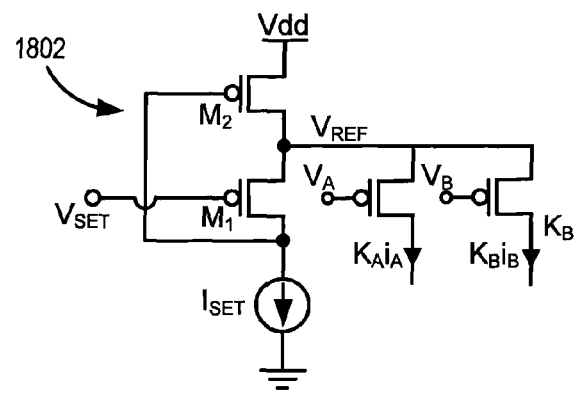
FIG. 18 is a schematic of a circuit for locally regenerating state variable currents from log-compressed voltages in accordance with the present invention.

Referring to FIG. 18, a flipped voltage follower circuit 1802 may be used to regenerate state variable currents. In this circuit, the transistor M2 and the current source $I_{SET}$ act as a common-source amplifier wrapped around a transistor M1 and small-signal impedance at the node $V_{REF}$ is reduced by the gain of this amplifier. That is, the gain drops from $1/g_{m1}$ to approximately $2/(g_{m1}g_{m2}r_{o1})$. In addition, this circuit can supply $V_{REF}$ with large amounts of current, but can only sink an amount $I_{SET}$. Thus, the flipped voltage follower provides a simple way of creating a variable, unidirectional power supply. It is contemplated that one of these circuits may be located within each reaction circuit and that a user may specify the values of the global variables $I_{SET}$ and $V_{SET}$ to fix the reference voltage $V_{REF}$. In addition, the user may set the global variables $I_{min}$ and $I_0$ for the reaction circuit. Each state variable can be regenerated by a PMOS transistor with its source tied to $V_{REF}$ and its gate tied to a given log-compressed, globally distributed voltage and the width of the transistor can be set by a DAC, thereby allowing its current to be programmably scaled. For example, the flipped voltage follower circuit 1802 shows that two state variables $i_A$ and $i_B$ have been regenerated with scaling factors $K_1$ and $K_2$, respectively.

Transistor mismatches, which are discussed above, can cause static errors in the local value of a given state variable and further cause errors in the rate constants and initial conditions assigned to a reaction. Thus, mismatch and device noise both act as sources of random variability in the behavior of reaction circuits. The dominant source of transistor mismatch is generally the threshold voltage $V_T$. A given voltage offset is exponentiated into a fractional error $(\Delta V_T/V_L)$ in the value of the state variable, where $V_L = \phi_T/\kappa \approx 37$ mV is the linear range of the transistor. Using a model of transistor mismatch between integrated MOS transistors it can, for example, be determined that the fractional error between two nominally-identical state variables increases when voltages are distributed across chips and locally exponentiated into circuits. An alternate strategy is to generate many copies of each current at one location, which reduces distances between transistors, and then distributing them across the chip. However, this leads to increased wiring, as many currents are distributed per state variable, instead of a single voltage. It is therefore contemplated that hybrid chip designs between these two extremes often provide the best tradeoff between accuracy and layout area.

Figure 19:
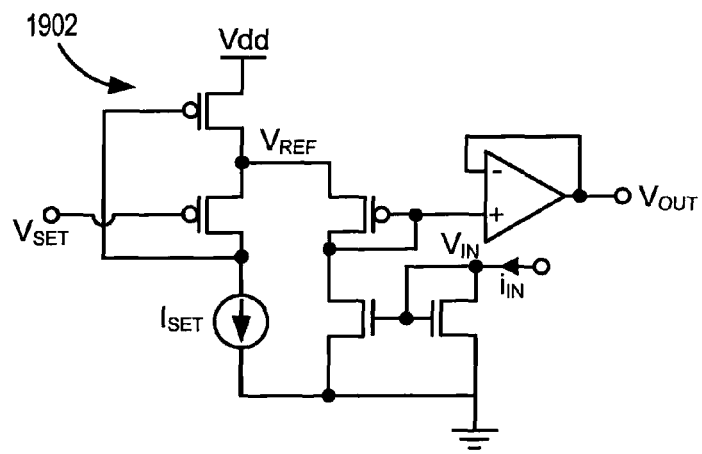
FIG. 19 is a schematic of a circuit that accepts an external current or voltage input and converts it into a suitable form for use on-chip in accordance with the present invention.
Figure 20:
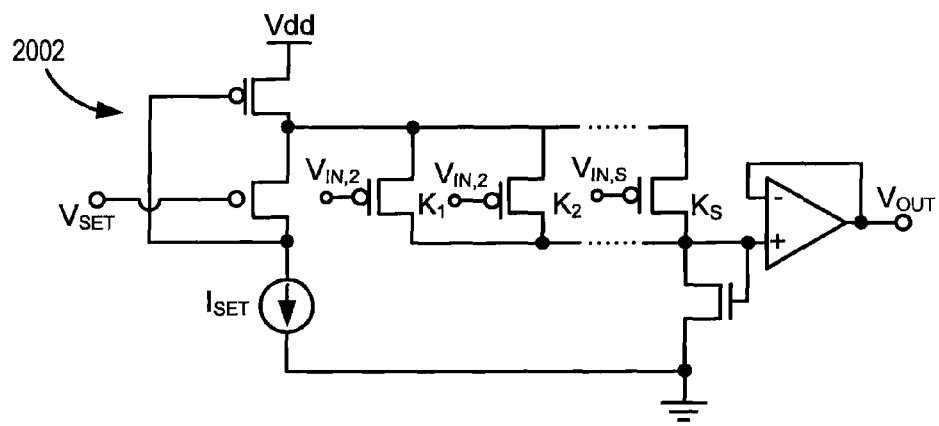
FIG. 20 is a schematic of a circuit that generates the weighted sum of multiple on-chip currents and converts it into a buffered, log-compressed voltage that can be sent of chip in accordance with the present invention.

Referring to FIG. 19, a circuit 1902 for feeding external inputs into a reaction simulation chip is shown. The reaction simulation chip may accept both currents $i_{IN}$ and log-compressed, ground-referenced voltages $V_{In}$ as inputs. A current mirror and a flipped voltage circuit are used to generate a $V_{REF}$-referenced voltage $V_{OUT}$ from $V_{IN}$. Therefore, the circuit sets $V_{OUT}$ such that the current through a standard-size PMOS transistor with its source at $V_{REF}$ and gate at $V_{OUT}$ is equal to $i_{IN}$. It can also be seen that the voltage $V_{OUT}$ is buffered by an operational amplifier before being fed to the rest of the chip. The buffer guarantees stability and rapid transient response when a single input is connected to many reaction circuits and therefore has a large capacitive load. Referring to FIG. 20, a circuit 2002 for generating outputs from a reaction simulation chip is shown. The output generation circuit 2002 implements one row of the output matrices H and K from the chemical reaction system of Eqn. 16. The electrical equivalent of Eqn. 16 is given by Eqn. 21 and shows that a single output is the weighted sum of all on-chip state variables and external inputs. It can be expected that most of weights are zero. Accordingly, the number of terms present in the summation can be restricted to S terms, where S is smaller than the total number of state variables and inputs, that is, $N+N_I$. Each input voltage $V_{IN,s}$ to the output generating circuit 2002 can be selected from the $N+N_I$ possible state variables and inputs by a connection matrix, or analog multiplexer. This connection matrix can be similar to a connection matrix used for connecting reaction circuits to state variables and inputs. The S transistors that convert these $V_{REF}$-referenced voltages into currents may actually represent 5-bit transistor DACs, wherein each DAC value $K_S$ can be individually set by a user. Further, the s-th transistor carries a current $K_s i_{IN,s}$ and, using KCL, the output current can be given by the following weighted sum:

$$i_{OUT} = \sum_{s=1}^{S} K_s i_{IN,s}. \qquad \text{Eqn. 61}$$

The current $i_{OUT}$ is log-compressed into a ground-reference voltage $v_{OUT}$ by an NMOS transistor before being buffered and taken off-chip. The buffer ensures that large capacitive loads, such as oscilloscope channels, can be driven with adequate bandwidth.

Figure 21:
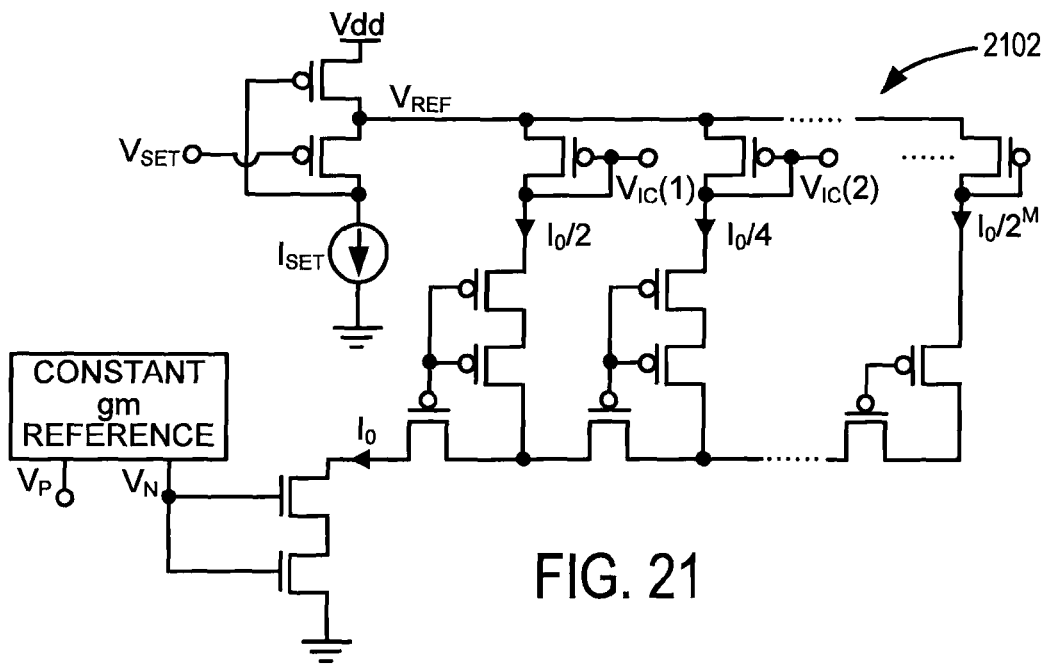
FIG. 21 is a schematic of a R-2R current divider circuit that generates DC voltages used for setting initial conditions in accordance with the present invention.

Referring to FIG. 21, a R-2R current divider circuit 2102 can be used to generate binary-weighted reference currents to set initial conditions for the reaction networks. The divider includes M stages, each with a lateral transistors and two series-connected transverse transistors. At every stage equal currents flow through the lateral and transverse transistors, thus resulting in binary splitting. The current splitting ratio at every stage is only determined by the geometries of the lateral and transverse transistors, which share the same source and gate voltages. Thus the circuit operates accurately both above and below threshold. The circuit also includes a termination stage having a transverse transistor that prevents an impedance discontinuity at the last stage and makes the splitter appear infinitely long.

The divider circuits 2102 accepts an input current $I_0$ generated on-chip by a constant-$g_m$ reference circuit and divides $I_0$ into M output currents, where the m-th current is given by $I_{IC}(n)=I_0 2^{-m}$, where m is an integer between 1 and M. In this circuit, each current is log-compressed and referenced to the reference voltage $V_{REF}$ to generate a set of voltages $V_{IC}$ that can be used to set initial conditions on the chip.

Figure 22:
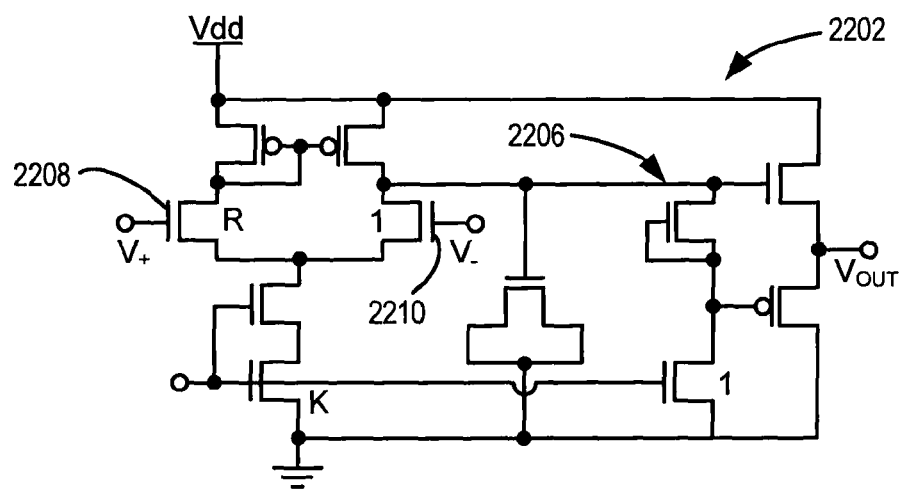
FIG. 22 is a schematic of a two-stage operational amplifier for buffering voltages used to set initial conditions and off-chip inputs in accordance with the present invention.

Referring to FIG. 22, a two-stage operational amplifier 2202 may be used in its unity-gain configuration to buffer voltages used to set initial conditions and off-chip inputs. The amplifier 2202 includes a class-AB push-pull output stage having low output impedance and high slew rate in both directions to provide low overshoot and rapid settling under conditions where the amplifier has to drive large capacitive loads. For example, this may occur when several state variables share the same initial condition so that their capacitors appear in parallel at the corresponding line within the initial condition bus. The amplifier also includes an auxiliary stage 2206 that sets the quiescent bias current of the output stage. This current is set by the current through the NMOS transistor, which is ratioed to be K times smaller than the tail current of the input stage $I_{BIAS}$. At the balance point, the input transistor 2208 connected to $v_+$ carries a current $I_{BIAS}(1+1/K)/2$, while the transistor 2210 connected to $v_-$ carries a current $I_{BIAS}(1+1/K)/2$. To prevent systematic offset these transistors should have the same $V_{GS}$ drop. To enforce this constraint the transistor 2208 connected to $v_+$ can be R times wider than the transistor 2210 connected to $v_-$, where the ratio R is given by $R=(K+1)/(K-1)$. For example, in a circuit with $K=4$, the ratio $R=5/3$. In addition, the circuit may include a MOS capacitor for internal compensation to save layout area and the tail current source may be self cascoded to increase its output performance. It is contemplated that the cascode includes a 3.3V I/O lower transistor having a higher threshold voltage than a 1.8V upper transistor, where the difference in threshold voltages provides enough $V_{DS}$ to keep the lower transistor saturated.

Figure 23:
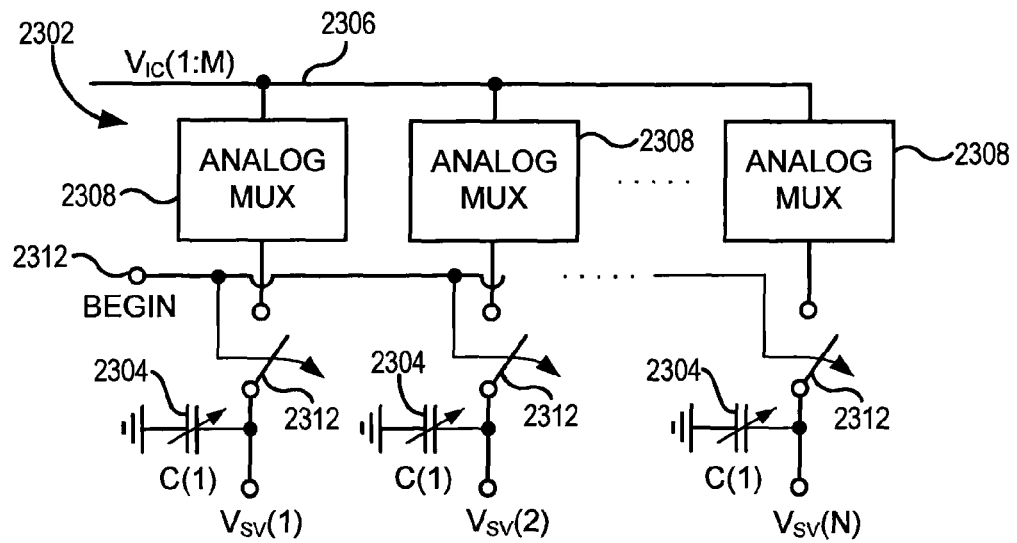
FIG. 23 is a schematic depiction of a scheme used on-chip for setting initial conditions in accordance with the present invention.

Referring to FIG. 23, a scheme that may be used on-chip for setting initial conditions is indicated generally at 2302. The chip includes the capacitors $C(1)$ to $C(N)$ 2304, which can each store a log-compressed state variable. The capacitors 2304 are actually implemented as the parallel combination of binary-weighted NMOS capacitors. It is contemplated that the value of each capacitor can be programmed by a user over a 5-bit range, for example, from 0.25 pF to 8 pF, to allow the simulation of multi-compartmental models. In addition, the capacitors can be connected to available initial condition voltages $V_{IC}$ 2306 through analog multiplexer circuits 2308, where, as described earlier, the voltages correspond to binary-weighted currents upon exponentiation.

The scheme 2302 includes a global control signal BEGIN 2310 that a user may raise to start a simulation. When BEGIN is high, series switches 2312 disconnect the initial conditions bus from the capacitors so the model's own dynamics can then set the voltages $V_{SV}$ on the capacitors $C(1)$ to $C(N)$. The BEGIN signal can also be used to trigger off-chip data acquisition equipment that records the simulation dynamics. Further, reaction circuits can be connected to external inputs rather than on-chip state variables, in which case the BEGIN signal does not disconnect the external inputs during a simulation.

Chip operating parameters may be programmed by a user through a three-wire bus having signals that can be denoted as CLK, DATA, and ENABLE. Bits on the DATA pin are loaded into an internal shift register at rising edges of the CLK signal. In the chemical reaction simulation chip 1702, for example, the global shift register is 180 bits long and includes three sections, as shown in Table 2.

TABLE 2

Structure of an on-chip shift register

| Bit Range | Function |
| --- | --- |
| 0-159 | Connection Matrix/Analog Multiplexers |
| 160-169 | Transistor and Capacitor DACs |
| 170-179 | Address |

Further, each reaction circuit, output generator, and state variable can include local memory and a unique 10-bit address so that local addresses can constantly be compared with the address bits stored within the global shift register. If the two addresses match and the ENABLE signal is high, then the shift register bits may be loaded into local memory. Therefore, to program the chip, a user may first send all 180 bits, including the address, on the DATA pin and the raise the ENABLE pin. This three-wire programming interface is relatively simple and extremely robust. The chip does not have to recover a clock from the data stream, because it is generated externally and is supplied on a separate pin. It should be noted that further modifications may be made to this design, especially to allowed improved interfacing of chips in accordance with the present invention to industry standard microcontrollers and other peripherals.

Figure 24:
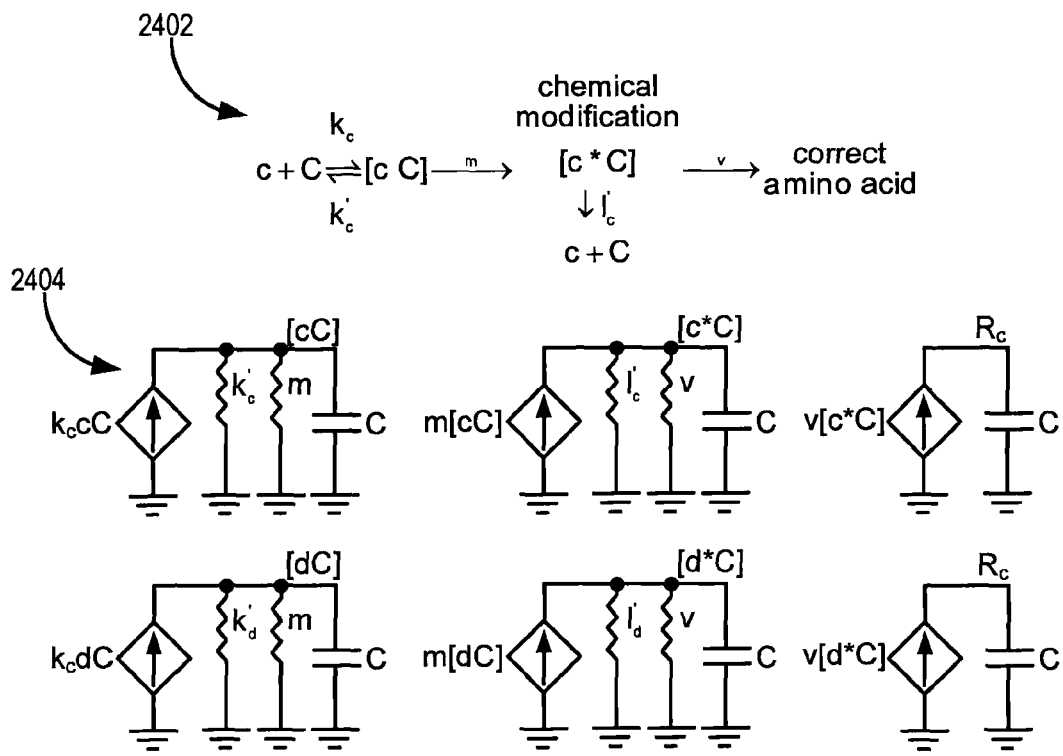
FIG. 24 shows the genetic process of kinetic proof reading to prevent mistranslation and its electronic analog in accordance with the present invention.

Referring to FIG. 24, an electronic system for modeling biochemical reactions can shed insight in biology that would otherwise be difficult to obtain. Circuit models are efficient for analyzing complex systems because they are inherently designed to graphically represent interactions between devices in a system in a meaningful way that lead to functional sub-blocks, which can parse complex systems into meaningful "network motifs" such as the FFL sub-block discussed above. For example, the language of circuits can provide a useful interpretation of "kinetic proof reading" circuits in cells, which are ubiquitously present in many cellular sub-systems. Kinetic proof reading allows a cell to reduce the discrimination error rate between highly similar molecules without great expenditure of time of cellular work. This biochemical process, which is depicted generally at 2402, includes a chemical-reaction cascade involved in the binding of a specific tRNA codon c with a three-letter snippet of RNA to a complimentary three-letter snippet in an mRNA molecule cC. This binding triggers events within the ribosome protein-translating machinery so the three-letter "codon word" in the mRNA is translated to an equivalent amino acid such that the sequence of letters in mRNA maps to an equivalent sequence of amino acids in the protein being constructed by the ribosome. To prevent translation errors, only the correct tRNA codon should bind to the mRNA so that incorrect amino acids are not incorporated into the protein. However, because two tRNA codons differing by only one letter have similar binding $K_d$'s, there is a relatively high probability of error. The error could be reduced with a more specific binding process. However, aside from being difficult to implement, this would cost time and lower the overall rate of translation, because the specificity of binding is determined by the rate of dissociation $k_c'$ rather than the association rate $k_c$, which is diffusion-limited and similar for all tRNA codons. High specificity would imply that each codon is bound for a long time due to a low $k_c'$, which would be prohibitive because the ribosome couldn't move on to translating other letter sequences until the bound tRNA codon dropped off the mRNA.

To reduce the error rate of translation, cells implement the methylation scheme depicted at 2402. The bound tRNA species cC is methylated by enzymes at a rate m to create the species c*C via a unidirectional reaction so that only the methylated species leads to translation at a unidirectional rate v. The affinity of the methylated tRNA codon for the mRNA is similar to that of the unmethylated tRNA such that the rate of dissociation $I_c'$ of the methylated species from the mRNA is proportional to $k_c'$ and high affinity tRNA codons bind longer to the mRNA, whether methylated or unmethylated. However, unlike the reversible binding of the $k_c/k_c'$ process, if the tRNA codon unbinds from the mRNA, it dissociates into an un-methylated form and cannot mount back onto the mRNA directly until it reforms cC. Because high-affinity tRNA codons are more likely to remain bound during the process of methylation and incorrect tRNA codons are more likely to dissociate, the methylation process is able to "screen" the translation process and significantly reduce mistranslation.

A circuit representation for this screening process is indicated generally at 2404. Similar circuits are shown for a tRNA codon c and a tRNA codon d with different rates of unbinding in methylated and unmethylated states. The tRNA codon c represents a true codon, while the tRNA codon d represents a codon that can falsely bind to the mRNA. From the circuits, it can be determined that the ratio of wrongly translated d, $R_d$, to correctly translated c, $R_c$, is given by an analysis of a two-stage "cascaded amplifier" topology as follows:

$$\frac{R_D}{R_C} = \frac{d}{c}\left(\frac{k_c' + m}{k_d' + m}\right)\left(\frac{l_c' + v}{l_d' + v}\right) \quad \text{Eqn. 62}$$

$$\approx \frac{d}{c}\left(\frac{k_c'}{k_d'}\right)\left(\frac{l_c'}{l_d'}\right)$$

$$= \frac{d}{c}\left(\frac{k_c'}{k_d'}\right)^2$$

where the approximation holds if $m \ll k_c'$ or $k_d'$, and $v \ll I_c'$ or $I_d'$. Typically, c and d are equally abundant such that $d/c \approx 1$. By having an additional stage of methylated amplification, the $R_d/R_c$ error rate can be improved from a linear dependence on $k_c'/k_d'$ to a square dependence on $k_c'/k_d'$, as seen in Eqn. 62. Thus, if $k_c'/k_d' = 10^{-2}$, then the mistranslation error rate is reduce to $10^{-4}$ because of the single methylation stage of amplification. If there are n stages of methylation, the ratio $R_c/R_d$ can be improved by a $(n+1)^{th}$ power law due to $(n+1)$ gain stages of amplification. Thus kinetic proof reading can be seen as analogous to improving the discriminability of one set of proportional resistances, that is, the c set, from another set of proportional resistances, that is, the d set, by including them in a multiple-gain-stage topology rather than a single-gain-stage topology. Since delays or time constants from multiple gain stages only add while gains multiply, kinetic proof reading exploits the energy-efficient principle of distributed-gain amplification.

In addition, the present invention may be employed to perform return-ratio robustness analyses of parameter and topology variations in a cell. Return ratio techniques allow the prediction of the closed-loop transfer function of a circuit when one of its parameters varies. More specifically, the relative change in a transfer function of a circuit, $d(TF_{gm})/TF_{gm}$, is related to the relative variation in the parameters of one its elements, such as $g_m$. This relationship may be expressed as follows:

$$\frac{d(TF_{gm})}{TF_{gm}} = \left(1 - \frac{TF_0}{TF_{gm}}\right)\left(\frac{dg_m/g_m}{1 + R_{inputnulled}}\right); \quad \text{Eqn. 63}$$

where $TF_0$ is the transfer function when $g_m = 0$ and $R_{input-nulled}$ is the return ratio of the element. As visible in FIGS. 4, 10, 15, and 16, variations in gene or protein parameters can be mapped to equivalent variations in circuit parameters. Eqn. 63 can therefore be used to predict how robust the circuit is to variations in a given circuit parameter. This analysis can provide insight into which gene and protein mutations and alterations significantly impact the performance of network and which do not. Similarly, return-ratio techniques can be employed to analyze the effect of "gene knockouts" where a whole node is deleted from the circuit. Such analyses can provide more subtle and robust models of error than digital-circuit techniques that model all DNA circuits as purely digital.

Therefore, a system and method for modeling chemical reactions is provided that utilizes exponential current-voltage devices to simulate chemical reaction events. When these exponential current-voltage devices are arranged on-chip in sets of translinear circuits, the present invention can be used to model large scale chemical and biochemical reaction networks that, for example, simulate the cellular processes of gene regulation and expression rapidly and in-parallel. Importantly, the stochastics of the chemical and biochemical processes are accurately included in such simulations. Thus, such simulation chips can be considered as "special purpose arithmetic logic units (ALUs)" that implement nonlinear dynamical systems optimized for simulating biochemical reaction networks. Accordingly, the present invention can be used to investigate biochemical systems by providing plausible ranges for unknown parameters in a reaction network based on simulations using known experimental data and constraints, simulating the effects of gene mutation and deletion, or testing the effects of a pharmacological agent on a biochemical pathway. Furthermore, the power of modern computation techniques can be brought to bear in investigating chemical and biochemical networks. For example, machine-learning techniques, such as stochastic gradient descent, regression, and gradient descent analysis, may be to analyze and configure the reaction simulation chips such that they optimize fits to experimental data, are consistent with known constraints, and maximize objective functions known to be of biological importance such as cell growth. Thus, the present invention provides a system capable of simulating and analyzing the biochemical processes that govern and define the life of a cell and, because intercellular communication is typically performed using biochemical reaction networks, the present invention further enables the study and simulation of higher-level functional groupings of cells and their response to factors such as drugs and pathogens.

The present invention has been described in terms of the preferred embodiment, and it should be appreciated that many equivalents, alternatives, variations, and modifications, aside from those expressly stated, are possible and within the scope of the invention. Therefore, the invention should not be limited to a particular described embodiment

The invention claimed is:

1. A method for simulating a chemical reaction using an electronic system comprising:
   providing an exponential current-voltage electronic device for modeling a chemical reaction event wherein:
      an electron concentration at an input of the exponential current-voltage electronic device is configured to model a concentration of a reactant in a chemical reaction event and an electron concentration at an output of the exponential current-voltage electronic device is configured to model a concentration of a product in the chemical reaction event;

a current flow through the exponential current-voltage electronic device is configured to model a rate of the chemical reaction event; and a voltage applied at a terminal of the exponential current-voltage electronic device is configured to model a free energy difference in the chemical reaction event;

applying a power characteristic at an input of the exponential current-voltage electronic device;

measuring a power characteristic at an output of the exponential current-voltage electronic device; and generating a report indicative of a chemical species concentration from the measured power characteristic.

2. The method as recited in claim 1 wherein the electronic system is a hardware system for simulating a chemical reaction.

3. The method as recited in claim 2 wherein at least one of a thermal and electronic shot noise of the exponential current-voltage electronic device is configured to model a stochastic behavior in the chemical reaction event.

4. The method as recited in claim 1 wherein pseudo-random noise for modeling a stochastic behavior in the chemical reaction event is introduced into the electronic system using a noise generation circuit.

5. The method as recited in claim 1 wherein the applied power characteristic is indicative of a reactant concentration in the chemical reaction event.

6. The method as recited in claim 1 further comprising applying a voltage or current to the exponential current-voltage electronic device to control the rate of current flow through the exponential current-voltage electronic device to control the rate of the chemical reaction event.

7. The method as recited in claim 6 wherein measuring the power characteristic indicative of the concentration of the product includes storing the power characteristic at a capacitor connected to the output of the exponential current-voltage electronic device and measuring a charge stored in the capacitor.

8. The method as recited in claim 6 wherein generating a report indicative of a chemical species concentration from the measured power characteristic includes employing the relationship:

$$\frac{x_i}{X_0} = \frac{i_i}{I_i}$$

in which $x_i$ is the chemical species concentration, $X_0$ is a global reference concentration, $i_i$ is a measured electrical current in the circuit, and $I_0$ is a global reference electrical current.

9. The method as recited in claim 1 further comprising:
providing a network comprising a plurality of the exponential current-voltage electronic devices for modeling a chemical reaction event;
simulating a network of chemical reactions by selectively applying power characteristics to selected inputs of the exponential current-voltage electronic devices;
measuring power characteristics at selected outputs of the exponential current-voltage electronic devices; and
generating a report indicative of a plurality of chemical species concentrations from each of the measured power characteristics.

10. The method as recited in claim 9 wherein at least a portion of the electronic exponential current-voltage devices are arranged in a translinear circuit.

11. The method as recited in claim 10 wherein the translinear reaction circuit is configured to simulate polynomial nonlinear reaction dynamics.

12. The method as recited in claim 11 wherein the reaction dynamics are at least one of zeroth, first, and second order.

13. The method as recited in claim 9 wherein logic-like interactions between the applied and measured power characteristics are simulated using a logic-like operations unit.

14. The method as recited in claim 9 wherein an efficacy of interaction between chemical species is simulated by employing combinational logic and memory to selectively control the applied and measured power characteristics.

15. The method as recited in claim 9 wherein time delays in the simulated chemical reaction network are modeled using a time delay circuit.

16. The method as recited in claim 9 wherein the chemical reaction network is a biochemical reaction network and the chemical species indicated in the report include at least one of inducers, transcription factors, genes, mRNA, and proteins.

17. The method as recited in claim 16 wherein a portion of the plurality of exponential current-voltage electronic devices are arranged in a programmable translinear circuit to simulate the genetic processes of transcription factor induction and binding.

18. The method as recited in claim 17 wherein another portion of the plurality of exponential current-voltage electronic devices are arranged in a programmable current-mode filter for simulating the genetic processes of transcription and translation.

19. The method as recited in claim 16 further comprising performing a return ratio robustness analysis by mapping variations in chemical species concentration to variations in power characteristics applied to selected exponential current-voltage electronic devices and analyzing the report indicative of chemical species concentration to simulate a response of the biochemical reaction network to the variations in chemical species concentration.

20. The method as recited in claim 17 wherein simulating a response of the biochemical reaction network to the variations in chemical species concentration includes simulating a response of the biochemical reaction network to at least one of gene alterations, gene knockouts, and protein alterations.

21. The method as recited in claim 17 wherein simulating a response of the biochemical reaction network to variations in chemical species concentration includes simulating at least one of changes in cellular operation associated with disease and changes in supracellular systems associated with disease.

22. The method as recited in claim 17 further comprising performing a return ratio robustness analysis that includes employing the relationship:

$$\frac{d(TF_{gm})}{TF_{gm}} = \left(1 - \frac{TF_0}{TF_{gm}}\right)\left(\frac{dg_m/g_m}{1 + R_{imputnulled}}\right)$$

in which $TF_{gm}$ is a transfer function of the electronic system, $g_m$ is a parameter of a component of the electronic system, and $TF_0$ is the transfer function of the electronic system when $g_m$ is zero.

23. An electronic system for modeling gene expression comprising:
- an induction module including at least one exponential current-voltage electronic device and configured to receive an input power characteristic indicative of a simulated concentration of a chemical species and simulate an activation of a transcription factor to produce an output power characteristic indicative of a concentration of the active transcription factor; and
- a transcription module including at least one exponential current-voltage electronic device and configured to receive the power characteristic indicative of a concentration of a transcription factor and simulate a genetic transcription process to produce an output power characteristic indicative of mRNA concentration.

24. The electronic system as recited in claim 23 wherein:
- an electron concentration at a first terminal of each exponential current-voltage device is configured to model a concentration of a reactant in a biochemical reaction event and an electron concentration at a second terminal of each exponential current-voltage device is configured to model a concentration of a product in the biochemical reaction event;
- a current flow through each exponential current-voltage device is configured to model a rate of the biochemical reaction event;
- a voltage applied at a third terminal of each exponential current-voltage device is configured to model a free energy difference in the biochemical reaction event; and
- an electronic shot noise in each exponential current-voltage electronic device is configured to model a stochastic behavior in the biochemical reaction event.

25. The electronic system of claim 23 further comprising a protein dynamics module including at least one exponential current-voltage electronic device and configured to receive the power characteristic indicative of mRNA concentration and simulate the genetic process of translation to produce a power characteristic indicative of a protein concentration.

26. The electronic system as recited in claim 25 further comprising an input module configured to receive instructions, set initial conditions, and produce the input power characteristic indicative of the concentration of the chemical species.

27. The electronic system as recited in claim 26 wherein the input module is further configured to produce power characteristics indicative of chemical species that are received by the protein dynamics module and regulate the simulated genetic process of translation.

28. The electronic system as recited in claim 27 wherein the power characteristic indicative of mRNA concentration and the power characteristic indicative of protein concentration are received by the induction module and regulate the simulated activation of transcription factors.

29. The electronic system as recited in claim 23 further comprising a time delay circuit connected to the transcription module and configured to simulate at least one of mRNA degradation, protein degradation, time delays in mRNA transcription, and time delays in protein translation.

30. The electronic system as recited in claim 23 wherein the transcription module further comprises a logic-like operations unit that receives a plurality of power characteristics indicative of active transcription factor and selectively combines the plurality of power characteristics indicative of active transcription factor concentration to simulate at least one of an activation and repression of a gene by a plurality of transcription factors.

31. The electronic system as recited in claim 30 wherein the logic-like operations unit is a generalized programmable logic array.

32. The electronic system as recited in claim 30 wherein simulating the activation of a gene by a plurality of transcription factors includes modeling activation functions having integer Hill coefficients.

33. The electronic system as recited in claim 23 wherein at least a portion of the exponential current-voltage electronic devices are arranged in translinear circuits.

34. The electronic system as recited in claim 33 wherein the exponential current-voltage electronic devices are at least one of bipolar junction transducers and metal oxide semiconductor field effect transistors operating in a subthreshold region.

35. The electronic system as recited in claim 33 wherein the translinear circuits simulate zeroth, first, and second order polynomial nonlinear reaction dynamics.

36. The electronic system as recited in claim 23 further comprising a noise generation circuit configured to produce pseudo-random noise for simulating a stochastic behavior of gene expression.

37. The electronic system as recited in claim 36 wherein the noise generation circuit is connected to the transcription module to create a stochastic variation in the power characteristic indicative of mRNA concentration.

38. The electronic system as recited in claim 36 wherein the noise generation circuit includes an exponential current-voltage electronic device, a current-controlled oscillator, at least one switch, and at least one of a random pulse generator, a random pulse generator based on a linear feedback shift register, a pseudo-random pulse generator, and a pseudo-random pulse generator based on a linear feedback shift register.

39. The electronic system as recited in claim 23 wherein mismatches between exponential current-voltage devices are reduced by applying at least one of an auto-zeroing technique and correlated-double sampling technique.

40. The electronic system as recited in claim 23 wherein a sensitivity analysis of gene expression is performed using feedback return-ratio analysis.

41. The electronic system as recited in claim 40 wherein the sensitivity analysis of gene expression includes detecting alterations in at least one of gene sequence and protein structure.

42. The electronic system as recited in claim 40 wherein the detected alterations in the at least one of gene sequence and protein structure are due to a simulated pharmacological agent.

43. An electronic system for modeling gene expression comprising:
- an input module configured to receive a power characteristic indicative of a mRNA concentration;
- a protein dynamics module including at least one exponential current-voltage electronic device and configured to receive the power characteristic indicative of mRNA concentration and simulate a genetic process of translation to produce a power characteristic indicative of a protein concentration; and
- an output module configured to receive the power characteristic indicative of protein concentration.

44. The electronic system as recited in claim 43 wherein:
- an electron concentration at a first terminal of each exponential current-voltage device is configured to model a concentration of a reactant in a biochemical reaction event and an electron concentration at a second terminal of each exponential current-voltage device is configured to model a concentration of a product in the biochemical reaction event;

a current flow through each exponential current-voltage device is configured to model a rate of the biochemical reaction event;

a voltage applied at a third terminal of each exponential current-voltage device is configured to model a free energy difference in the biochemical reaction event; and an electronic shot noise in each exponential current-voltage electronic device is configured to model a stochastic behavior in the biochemical reaction event.

45. The electronic system as recited in claim 44 further comprising:

an induction module including at least one exponential current-voltage electronic device and configured to receive an input power characteristic indicative of a simulated concentration of a chemical species and simulate an activation of a transcription factor to produce an output power characteristic indicative of a concentration of the active transcription factor; and a transcription module including at least one exponential current-voltage electronic device and configured to receive the power characteristic indicative of a concentration of a transcription factor and simulate a genetic transcription process to produce the power characteristic indicative of mRNA concentration.

46. The electronic system as recited in claim 45 further comprising a time delay circuit connected to the transcription module and configured to simulate at least one of mRNA degradation, protein degradation, time delays in mRNA transcription, and time delays in protein translation.

47. The electronic system as recited in claim 45 wherein the input module is configured to receive instructions, set initial conditions, and produce the input power characteristic indicative of the simulated concentration of the chemical species.

48. The electronic system as recited in claim 47 wherein the input module is further configured to produce power characteristics indicative of chemical species that are received by the protein dynamics module and regulate the simulated genetic process of translation.

49. The electronic system as recited in claim 48 wherein the power characteristic indicative of mRNA concentration and the power characteristic indicative of protein concentration are received by the induction module and regulate the simulated activation of transcription factors.

50. The electronic system as recited in claim 45 wherein the transcription module further comprises a logic-like operations unit that receives a plurality of power characteristics indicative of active transcription factor concentration and selectively combines the plurality of power characteristics indicative of active transcription factor concentration to simulate at least one of an activation and repression of a gene by a plurality of transcription factors.

51. The electronic system as recited in claim 50 wherein the logic-like operations unit is a generalized programmable logic array.

52. The electronic system as recited in claim 50 wherein simulating the activation of a gene by a plurality of transcription factors includes modeling activation functions having integer Hill coefficients.

53. The electronic system as recited in claim 43 wherein at least a portion of the exponential current-voltage electronic devices are arranged in translinear circuits.

54. The electronic system as recited in claim 53 wherein the exponential current-voltage electronic devices are at least one of bipolar junction transducers and metal oxide semiconductor field effect transistors operating in a subthreshold region.

55. The electronic system as recited in claim 53 wherein the translinear circuits simulate zeroth, first, and second order polynomial nonlinear reaction dynamics.

56. The electronic system as recited in claim 43 further comprising a noise generation circuit configured to produce pseudo-random noise for simulating a stochastic behavior of gene expression.

57. The electronic system as recited in claim 56 wherein the noise generation circuit is connected to the transcription module to create a stochastic variation in the power characteristic indicative of mRNA concentration.

58. The electronic system as recited in claim 56 wherein the noise generation circuit includes an exponential current-voltage electronic device, a current-controlled oscillator, at least one switch, and at least one of a random pulse generator, a random pulse generator based on a linear feedback shift register, a pseudo-random pulse generator, and a pseudo-random pulse generator based on a linear feedback shift register.

59. The electronic system as recited in claim 43 wherein mismatches between exponential current-voltage devices are reduced by applying at least one of an auto-zeroing technique and correlated-double sampling technique.

60. The electronic system as recited in claim 43 wherein a sensitivity analysis of gene expression is performed using feedback return-ratio analysis.

61. The electronic system as recited in claim 60 wherein the sensitivity analysis of gene expression includes detecting alterations in at least one of gene sequence and protein structure.

62. The electronic system as recited in claim 61 wherein the detected alterations in the at least one of gene sequence and protein structure are due to a simulated pharmacological agent.

63. An electronic system configured to simulate noise in a biochemical reaction network comprising:

a current mode integrator configured to receive an input signal;

a current leakage circuit connected to the current mode integrator and configured to produce a leak current; and a control feedback circuit connected to the current leakage circuit and configured to pseudo-randomly control the leak current.

64. The electronic system as recited in claim 63 wherein the control feedback circuit includes at least one of a current-controlled oscillator, an exponentiator, and at least one of a random pulse generator, a random pulse generator based on a linear feedback shift register, a pseudo-random pulse generator, and a pseudo-random pulse generator based on a linear feedback shift register.

65. The electronic system as recited in claim 63 wherein the current leakage circuit and the control feedback circuit are connected via a switch that is gated by the control feedback circuit and configured to alter the leak current.

66. The electronic system as recited in claim 63 wherein leak current is received by an electronic system for simulating chemical reactions to introduce pseudo-random Poisson noise to the electronic system for simulating chemical reactions.

* * * * *